United States Patent [19]
Higuchi et al.

[11] 3,986,510
[45] Oct. 19, 1976

[54] BIOERODIBLE OCULAR DEVICE

[75] Inventors: Takeru Higuchi; Anwar A. Hussain, both of Lawrence, Kans.; John W. Shell, Los Altos, Calif.

[73] Assignee: Alza Corporation, Palo Alto, Calif.

[22] Filed: Aug. 1, 1975

[21] Appl. No.: 601,154

Related U.S. Application Data

[62] Division of Ser. No. 179,129, Sept. 9, 1971, abandoned.

[52] U.S. Cl. .................................. 128/260; 424/16; 424/19; 128/130
[51] Int. Cl.² ...................... A61M 31/00; A61F 5/46
[58] Field of Search ................. 128/260, 271, 335.5, 128/268, 272, 130; 424/16, 37, 33, 19

[56] References Cited
UNITED STATES PATENTS

| | | | |
|---|---|---|---|
| 273,410 | 3/1883 | Wadleigh | 128/271 |
| 3,113,076 | 12/1963 | Jacobs | 128/272 X |
| 3,249,109 | 5/1966 | Maeth et al. | 128/268 |
| 3,297,033 | 1/1967 | Schmitt et al. | 128/335.5 |
| 3,329,574 | 7/1967 | Barrow et al. | 424/37 |
| 3,444,858 | 5/1969 | Russell | 128/268 X |
| 3,574,820 | 4/1971 | Johnson et al. | 424/37 |
| 3,598,122 | 8/1971 | Zaffaroni | 128/268 |
| 3,598,123 | 8/1971 | Zaffaroni | 128/268 |
| 3,618,604 | 11/1971 | Ness | 128/260 |
| 3,625,214 | 12/1971 | Higuchi | 128/260 |
| 3,630,200 | 12/1971 | Higuchi | 128/260 |
| 3,640,741 | 2/1972 | Etes | 424/33 X |
| 3,641,237 | 2/1972 | Gould et al. | 424/16 |
| 3,773,919 | 11/1973 | Boswell | 128/260 X |

FOREIGN PATENTS OR APPLICATIONS

| | | | |
|---|---|---|---|
| 1,003,914 | 3/1957 | Germany | 128/260 |

OTHER PUBLICATIONS

"Polyvinyl Alcohol Films in the Therapy of Eye Infections;" Yu F. Maichuk, Antibiotiki 12, No. 5, pp. 432–435 (1967).
"Use of Pilocarpine Impregnated Alcohol Films in the Treatment of Glnacomatous Patients;" Iakovlev and Lenkevitch, Vestn. Oftal. 79, pp. 40–42 (Nov.–Dec. 1966).
"Gelatin as an Absorbable Implant in Scleral Buckling Procedures", Arch Opthal, vol. 79, pp. 286–290, (1968).
"Possibilities of Application of Eye Drugs with the Aid of Gel Contact Lenses", Cs. Cftalmologie, vol. 21, No. 6, pp. 509–512, (1965).

*Primary Examiner*—Aldrich F. Medbery
*Attorney, Agent, or Firm*—Thomas E. Ciotti; Paul L. Sabatine; Edward L. Mandell

[57] ABSTRACT

An ocular insert for the continuous controlled administration of a predetermined therapeutically effective dosage of drug to the eye over a prolonged period of time. The device meters the flow of drug by means of a drug release rate controlling material. The insert bioerodes in the environment of the eye concurrently with the dispensing or at a point in time after the dispensing of the therapeutically desired amount of drug.

5 Claims, 7 Drawing Figures

BIOERODIBLE OCULAR DEVICE

This is a division of application Ser. No. 179,129, filed Sept. 9, 1971 and now abandoned.

BACKGROUND OF THE INVENTION

This invention relates to a method and device for the controlled continuous administration of drug to the eye over a prolonged period of time. Still more particularly, this invention relates to an ocular drug device capable of bioeroding in the environment of the eye concurrently with the dispensing or at a point in time after the desired amount of drug has been administered.

Presently, diseases of the eye are still conventionally treated by periodically applying ophthalmic drugs in liquid or ointment form. While this method of administration is suitable in certain instances, a serious shortcoming is the failure of these types of dosage formulations to dispense the drug in a continuous manner. Periodic application of these dosage forms, even though they be applied at intervals during the day and night, results in the eye receiving a massive, but unpredictable, amount of drug at each time of application. The result of this intermittent administration is that the level of drug surges to a peak at the time the drug is applied to the eye, followed by a decline in concentration. Thus, a plot of drug in the eye and surrounding tissues vs time, after administration of several dosage forms a day has the appearance of a series of peaks which may surpass the toxic threshold of the drug and valleys which fall below the critical point needed to achieve the desired therapeutic effect. Further, drug administered via an ointment or liquid form of therapy is washed away rapidly by tear fluid, leaving the eye without medication until the next application. Moreover, in some ocular conditions characterized by constant deterioration, i.e. glaucoma, continuous treatment offers extremely important therapeutic advantages. Most ointment dosage forms presently available are in unsterilized form, and are generally difficult to use without impairment of vision.

It was proposed, late last century, to use water soluble drug containing gels of glycerinated gelatin that are shaped to the form of a lamella or eye disk. Such lamellae are applied to the eye to supply drug thereto. In use, the glycerinated gelatin vehicle dissolves almost instantly in tear liquid, producing the same type of effect as do liquid dosage forms. Thus, these disks are not suitable for providing for prolonged or sustained continuous release of a drug because of their rapid rate of dissolution. Further information on these water soluble dosage forms can be found in *Remington's Pharmaceutical Sciences, XIII*, pp. 547–8 (Mack Publishing Co., Easton, Pa., 1965); Fishburn, *An Introduction to Pharmaceutical Formulation*, p. 116 (Pergman Press Ltd., New York City, N.Y., 1965); and U.S. Pat. No. 273,410, Mar. 6, 1883.

Recognizing these disadvantages, a significant advance has recently been made in the field of ophthalmic drug delivery systems. In this regard, U.S. Pat. No. 3,416,530, granted Dec. 17, 1968, entitled "Eyeball Medication Dispensing Tablet", and Ser. No. 831,761, filed June 9, 1969, entitled "Ocular Insert", disclose a drug dispensing ocular insert which slowly releases drug to the eye for prolonged periods of time. Such ocular inserts are fabricated of materials that are biologically inert, non-allergenic, and insoluble in tear liquid. To initiate the therapeutic program, the ocular insert is placed in the upper or lower sac of the eye bounded by the surfaces of the sclera of the eyeball and conjunctiva of the lid. Since the material from which the ocular insert is formed is insoluble in tear liquid, it retains its integrity and remains intact during the course of therapy, acting as a reservoir to continuously release drug to the eye and surrounding tissues at a controlled rate. On termination of the therapeutic program the ocular insert is removed from the eye. Thus, a single such ocular insert provides the complete ophthalmic dosage regimen for a particular time period, on the order of 24 hours or longer. More frequent repeated applications which are necessary with liquids, ointments, or water soluble lamellae are avoided.

While the drug dispensing ocular inserts described above, which deliver drug to the eye continuously and in a controlled manner over a prolonged period of time, have proved to be markedly superior to the prior art ointments and liquids, there remain, however, improvements to be made. The ocular insert, after insertion in the eye sac, is designed to remain intact during the course of therapy, and does so since it is formed of material insoluble in tear liquid. On termination of the therapy program the insert must be removed, which may present difficulty and discomfort to some patients. In rare instances, the simple removal if made more difficult by unwanted migration of the insert to the upper fornix, where it may remain long after the entire drug supply has been released to the eye. Further, as is often conventional in ophthalmic practice, physician-patient contact is not of a sufficient degree so as to insure that medical instructions from the doctor are accurately carried out by the patient. Thus, in the case of the use of an insoluble ocular insert, there is no certainty that the patient will remove the device when scheduled to do so. This is particularly true with elderly patients who often forget or are simply unable to remove the device due to failing memory or eyesight.

SUMMARY OF THE INVENTION

Accordingly, it is an object of this invention to provide an improved drug dispensing ocular insert for the controlled continuous administration of drugs to the eye over a prolonged period of time.

Still another object of this invention is to provide an improved drug dispensing ocular insert which does not have to be removed from the eye after termination of the therapeutic program.

A further object of this invention is to provide an improved method for treating diseases of the eye.

Another object of this invention is to provide an improved drug dispensing ocular insert for delivering drugs to the eye with increased efficacy.

A still further object of this invention is to provide a bioerodible ocular device which can be adapted to medications having either relatively high or relatively low solubilities in eye fluids.

In accomplishing these objects, a major aspect of this invention resides in an ocular insert for the controlled continuous administration of a predetermined dosage of drug to the eye, comprising one or more reservoirs, each of the reservoirs comprised of a drug formulation confined within a bioerodible drug release rate controlling material, the insert being of an initial shape which is adapted for insertion and retention in the sac of the eye bounded by the surfaces of the bulbar conjunctiva of the sclera of the eyeball and the palpebral conjunctiva of the lid, the material continuously metering the flow of a therapeutically effective amount of drug from the reservoir to the eye at a controlled rate over a prolonged period of time, and wherein the insert bioerodes in the environment of the eye concurrently with the dispensing or at a point in time after the dispensing of the therapeutically desired amount of drug.

One embodiment of the invention described above resides in an ocular insert for the controlled continuous administration of a predetermined dosage of drug to the eye over a prolonged period of time, comrising a body of bioerodible drug release rate controlling material containing a drug formulation confined therein, the body being of an initial shape which is adapted for insertion and retention in the sac of the eye bounded by the surfaces of the bulbar conjunctiva of the sclera of the eyeball and the palpebral conjunctiva of the lid, the body continuously metering the flow of a therapeutically effective amount of drug to the eye at a controlled rate over a prolonged period of time, and wherein the body bioerodes in the environment of the eye concurrently with the dispensing or at a point in time after the dispensing of the therapeutically desired amount of drug.

In another aspect, this invention resides in an ocular insert for the controlled continuous administration of a predetermined dosage of drug to the eye, comprising (1) an inner reservoir containing a drug formulation confined therein, and (2) an outer membrane formed from drug release rate controlling bioerodible material surrounding the inner reservoir, the membrane being permeable to passage of drug, but at a lower rate than through the inner reservoir, the insert being of an initial shape which is adapted for insertion and retention in the sac of the eye bounded by the surfaces of the bulbar conjunctiva of the sclera of the eyeball and the palpebral conjunctiva of the lid, the outer membrane material continuously metering the flow of a therapeutically effective amount of drug from the reservoir to the eye at a controlled rate over a prolonged period of time, and wherein the insert bioerodes in the environment of the eye concurrently with the dispensing or at a point in time after the dispensing of the therapeutically desired amount of drug.

In still another aspect, this invention resides in an ocular insert for the controlled continuous administration of a predetermined dosage of drug to the eye over a prolonged period of time, comprising a plurality of reservoirs, each of the reservoirs comprised of a drug formulation confined within a drug release rate controlling material, the reservoirs characterized by being either:

1. a microcapsule of an initial size and configuration such as to be capable of being eliminated from the ocular cavity through the punctum with tear fluid, or
2. a microcapsule of bioerodible material; the reservoirs being distributed throughout a bioerodible matrix material permeable to the passage of drug at a higher rate than through the drug release rate controlling material, the latter material metering a therapeutically effective amount of drug from the reservoir to the eye at a controlled rate over a prolonged period of time, the insert being of an initial shape which is adapted for insertion and retention in the sac of the eye bounded by the surfaces of the bulbar conjunctiva of the sclera of the eyeball and the palpebral conjunctiva of the lid, and wherein the reservoir and matrix are eliminated from the ocular cavity by bioeroding in the environment of the eye or the reservoir eliminated by passage through the punctum, the elimination taking place concurrently with the dispensing or at a point in time after the dispensing of the therapeutically desired amount of drug.

Other objects, features and advantages of the invention will become more apparent from the following description when taken in conjunction with the drawings and from the claims.

DETAILED DESCRIPTION OF THE INVENTION

The term "bioerodible", as used in the specification and claims, is defined as the property or characteristic of a body of a microporous, solid or gel material to innocuously disintegrate or break down as a unit structure or entity, over a prolonged period of time, in response to the environment in the eye by one or more physical or chemical degradative processes, for example by enzymatic action, oxidation or reduction, hydrolysis (proteolysis), displacement, e.g. ion exchange, or dissolution by solubilization, emulsion or micelle formation, and which material is thereafter absorbed by the eye and surrounding tissues, or otherwise dissipated, such as by elimination from the ocular cavity through the punctum with tear fluid.

As used in the instant specification and appended claim, the term "prolonged period of time" is meant to include time intervals of from at least 8 hours to approximately 30 days or higher and preferably periods of from 1 to 8 days. It should be noted that this term is applied with reference to the time interval over which the drug is released and also with reference to the time interval over which the insert and component materials bioerode in the environment in the eye, although each of the aforesaid time periods may not necessarily be concurrently coextensive in duration.

The term "reservoir", as used herein to define the drug-containing portion of the ocular insert, is intended to connote a broad class of structures capable of fulfilling the intended function and, as will be hereinafter more completely developed, includes a plurality of discrete, drug-containing microcapsules or a porous, hollow, solid, gel or liquid drug-containing body of material. The microcapsule can be formed as a hollow container having the drug therein or be formed as a solid or porous particle having the drug distributed therethrough.

In accordance with the present invention, there is provided an ocular insert for the controlled continuous dispensing of a predetermined dosage of drug to the eye over a prolonged period of time, comprising one or more reservoirs, each of the reservoirs comprised of a drug formulation confined within a bioerodible drug release rate controlling material, the insert being of an initial shape which is adapted for insertion and retention in the sac of the eye bounded by the surfaces of the bulbar conjunctiva of the sclera of the eyeball and the palpebral conjunctiva of the lid, the material continuously metering the flow of a therapeutically effective amount of drug from the reservoir to the eye at a controlled rate over a prolonged period of time, and wherein the insert bioerodes in the environment of the eye concurrently with the dispensing or at a point in time after the dispensing of the therapeutically desired amount of drug.

Figure 1:
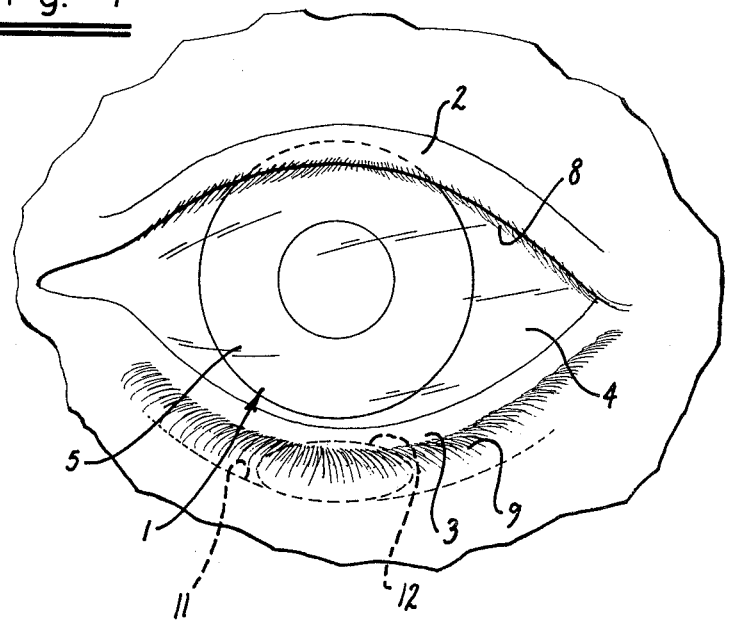
FIG. 1 is a view partly in front elevation and partly diagrammatic of a human eye, illustrating an ocular insert of this invention is an operative position soon after insertion in the eye.
Figure 2:
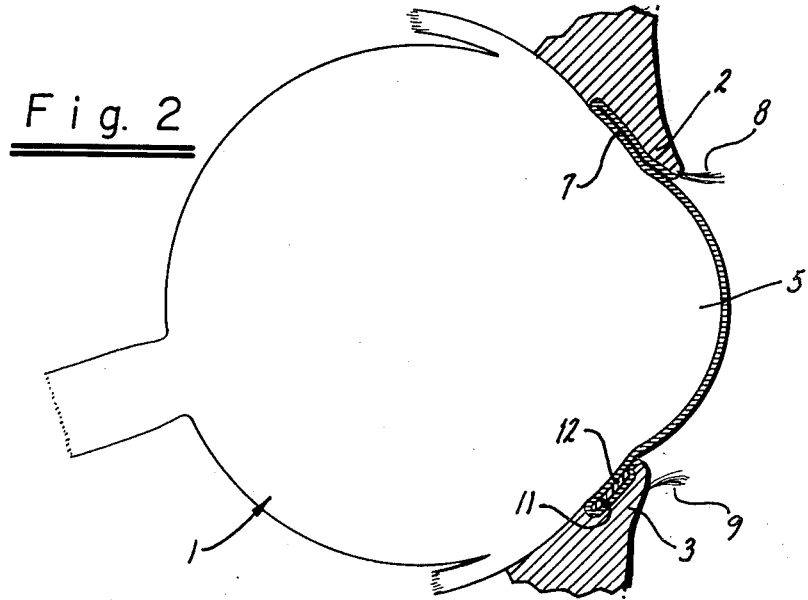
FIG. 2 is a view partly in vertical section and partly diagrammatic of an eyeball and the upper and lower eyelids associated therewith showing the ocular insert of this invention in operative position.

Referring particularly to FIGS. 1 and 2, a human eye is shown, more or less diagrammatically, as comprising an eyeball 1 and upper and lower eyelids 2 and 3, respectively, the eyeball 1 being covered for the greater parts of its area by the sclera 4 and at its central portion by the cornea 5. The eyelids 2 and 3 are lined with an epithelial membrane or palpebral conjunctiva. The sclera 4 is also lined with an epithelial membrane or bulbar conjunctiva which covers the exposed portion of the eyeball including the cornea 5, that portion covering the cornea being transparent; that portion of the palpebral conjunctiva which lines the upper eyelids 2 and the underlying portion of the bulbar conjunctiva defining the upper sac 7 and that portion of the palpebral conjunctiva which lines the lower eyelid 3 and the underlying portion of the bulbar conjunctiva defining the lower sac 11. Upper and lower eyelashes are indicated at 8 and 9, respectively.

An ocular insert 12 is shown in operative position in the lower sac 11 of the eye. Other details of the eyeball 1 are not directly concerned with the structure of the instant invention and, therefore, details showing the description thereof are being omitted in the interest of brevity.

To use the ocular insert of the invention, as illustrated in FIGS. 3, 4, 5 and 6, it is inserted within the upper 7 or lower sac 11. Placement in the lower sac is preferred due to the tendency of the eye to roll upwardly during sleeping, known as Bell's phenomenon, which may cause discomfort to some patients if the insert is located in the upper sac 7. The ocular device illustrated in FIG. 7 is inserted in the area surrounding the corneal surface of the eye lying in both the upper and lower sacs 7 and 11.

Once in place, the ocular insert functions to continuously administer a metered amount of drug from the reservoir to the eye and surrounding tissues over a prolonged period of time through the primary drug transfer mechanisms of: (1) "Permeation Control Release", i.e. the controlled release of the drug by the processes of: (a) diffusive transfer by controlled flow of drug through the rate controlling material of the insert, and/or (2) "Erosion Control Release", i.e. the metered release of entrapped drug contained in the release rate controlling material as the material bioerodes in a controlled and predetermined manner over a prolonged period of time in response to the action of the environment in the eye. It will be understood with regard to mechanism (1) above, i.e. Permeation Control Release, that the rate controlling material can be either of an imperforate or microporous nature, and therefore flow of drug can be effected by molecular diffusion as is the mode in the case of imperforate rate controlling materials, or by viscous diffusive flow as is the mode in the case of microporous rate controlling materials which are impregnated with eye fluids. Both of these modes of drug transfer are intended to be included herein. It is further intended to include as microporous material hydrophilic materials which may be initially imperforate, but which swell and become microporous in structure in the environment of the eye. In any event, after the drug leaves the ocular insert, it is transported to the eye and surrounding tissues, including the corneal epithalium, by the flow of tear liquid and the blinking action of the eyelids.

Any material having the ability to control the rate of release of drug over a prolonged period of time by either of these mechanisms, or a combination of these mechanisms, (1) or (2) above, is herein defined as "drug release rate controlling material".

Another mechanism for drug release which must be considered in the case of inserts made from water permeable materials and water soluble drugs is that of simple dissolution of the drug, as for example by leaching. Release of drug by this mode is not preferred due to the fact that it is difficult to control.

Figure 3:
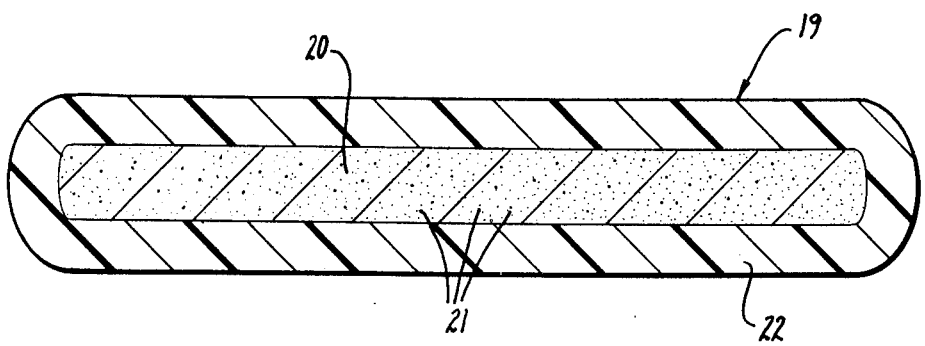
FIGS. 3, 4, 5, 6 and 7 are cross-sectional views of several embodiments of ocular inserts of this invention.
Figure 4:
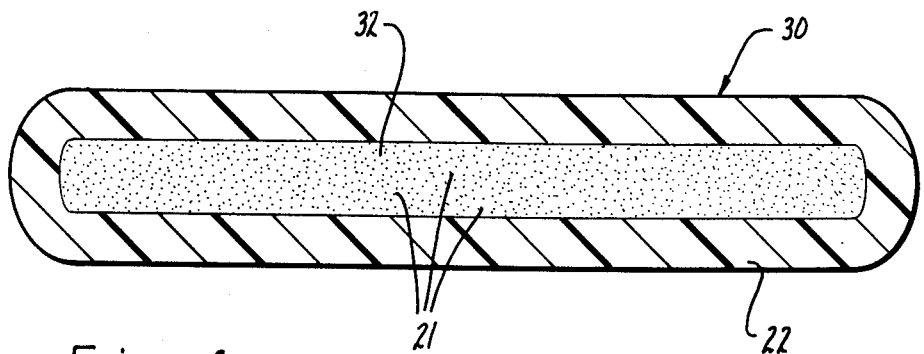
Figure 5:
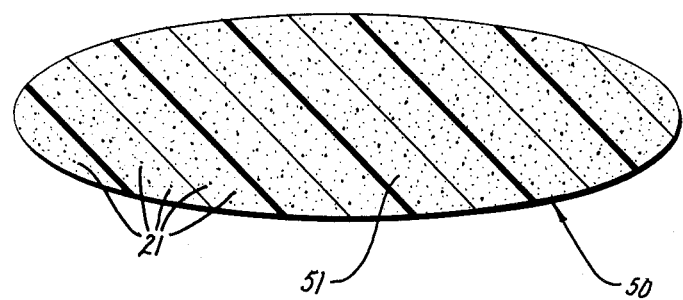

Depending upon the particular embodiment, the drug reservoir can be of drug release rate controlling material or otherwise. However, as is apparent in the latter case, the drug must first pass through drug release rate controlling material prior to reaching the eye. It is therefore critical to the practice of this invention for all embodiments that the drug pass through the drug release rate controlling material to meter the flow thereof at some point after or concurrent with the release of drug from the reservoir and prior to reaching the eye. The drug release rate controlling material can be of the barrier or membrane type for example as shown in FIGS. 3 or 4, or of the matrix type for example as shown in FIG. 5.

It has been found that the ocular insert of this invention provides several important advantages over known devices and methods of administering drugs to the eye. One important advantage of the claimed insert resides in the fact that, in addition to the ability to effectively control the amount of drug dispensed in a continuous manner and over a prolonged time span with the attendant advantages thereto, it is not necessary for the patient to remove the device from the eye at the termination of the therapeutic program as a result of its bioerodible characteristics. Thus, the devices of this invention lend themselves to the obtainment of the benefits of continuous administration and also minimize the disadvantages of having to remove the ocular insert from the eye. This latter aspect is a particularly important feature since, by the very nature of the anatomy involved, tasks such as removal of an object from the eye are made increasingly more difficult. Moreover, risks of patient non-compliance with medical instructions, a well known factor in ophthalmic practice, are minimized to a large degree by the inherent drug administration pre-program dosage and terminating capabilities of the devices of this invention.

Yet, another important advantage of the devices of this invention resides in the ability to effectively control the rate of release of drug in a zero order manner, that is, the rate of release of drug is substantially independent of time throughout the major portion of the administration period. This aspect further enhances the therapeutic benefits to be obtained by insuring that the drug is both continuously available and at substantially the same dosage rate. Alternatively, drug can be administered from the device according to other predetermined time release patterns. One embodiment that is particularly suited to provide drug release patterns that are for example sinusoidal, parabolic, and the like, is that illustrated in FIG. 6. As more fully described hereinafter, varying release patterns can be obtained by appropriate selection of reservoirs having different drug release rate characteristics for use in a given ocular insert.

Still another benefit to be derived by use of the instantly claimed insert is the increased therapeutic efficacy per unit amount of drug administered.

The ocular insert can be fabricated in any convenient shape for comfortable retention in the sac of the eye. Thus, the marginal outline of the ocular insert can be ellipsoid, donut-shape, bean-shape, banana-shape, circular, rectangular, etc. In cross-section, it can be doubly convex, concavo-convex, rectangular, etc. as the ocular insert in use will tend to conform to the configuration of the eye, the original cross-sectional shape of the device is not of controlling importance. Dimensions of the device can vary widely. The lower limit on the size of the device is governed by the amount of the particular drug to be supplied to the eye and surrounding tissues to elicit the desired pharmacologic response, as well as by the smallest sized device which conveniently can be inserted in the eye. The upper limit on the size of the device is governed by the geometric space limitations in the eye, consistent with comfortable retention of the ocular insert. Satisfactory results can be obtained with an ocular device for insertion in the sac of the eye of from 4 to 20 millimeters in length, 1 to 12 millimeters in width, and 0.1 to 2 millimeters in thickness. Several embodiments of these inserts are exemplified in FIGS. 3 through 7, inclusive.

In one aspect of this invention, as illustrated in FIGS. 3 and 4, the ocular insert comprises (1) an inner reservoir containing a drug formulation confined therein, and (2) an outer membrane formed from drug release rate controlling bioerodible material surrounding the inner reservoir, the membrane being permeable to passage of drug, but at a lower rate than through the inner reservoir, the insert being of an initial shape which is adapted for insertion and retention in the sac of the eye bounded by the surfaces of the bulbar conjunctiva of the sclera of the eyeball and the palpebral conjunctiva of the lid, the outer membrane material continuously metering the flow of a therapeutically effective amount of drug from the reservoir to the eye at a controlled rate over a prolonged period of time, and wherein the insert bioerodes in the environment of the eye concurrently with the dispensing or at a point in time after the dispensing of the therapeutically desired amount of drug.

FIG. 3 illustrates generally, by reference numeral 19, an embodiment of this invention wherein the bioerodible ocular insert is comprised of an inner reservoir 20 which is formed of a bioerodible matrix material having drug 21 dispersed therethrough. Surrounding matrix 20 is a rate controlling membrane 22 which is also bioerodible in the eye. Both matrix 20 and membrane 22 are permeable to the passage of drug by diffusion, that is, molecules of the drug can dissolve in and diffuse through these materials; however, the permeability of membrane 22 to drug is lower than from the matrix 20 so that release of drug through membrane 22 is the drug rate release controlling step from the ocular insert. The inner matrix 20 serves as a depot or reservoir source for the drug and can be a porous, solid or gel material. Drug molecules move through the inner matrix 20 by diffusion, thereby uniformly saturating the innermost surface of membrane 22 with drug after equilibrium conditions are reached. Drug is continuously metered through and removed from the outer surface of membrane 22 where it is made available to the eye fluids and tissues.

An advantage of the insert of the type illustrated in FIG. 3 is that it can be adapted to release drug in a zero order manner, that is, at a constant rate and over a prolonged period of time. By the appropriate design and selection of materials, drug release from the device is preferably primarily effected by a "permeation control release mechanism" and includes a sequence of steps characterized by controlled drug diffusion through membrane 22 followed by a combination of leaching of drug by the tear liquid and the blinking action of the eyelids in order to transport the drug from the outermost surface of membrane 22 to the eye and surrounding tissues. Release rate is controlled by system variables such as the diffusivity and solubility of the drug in the membrane material 22 and the thickness of this material. Design of an ocular device, therefore, necessitates selection of materials and other parameters in order to provide the proper release rates and dosage regimen, depending upon the particular drug to be used. The following are generalized considerations in order to properly design an ocular insert of the type illustrated in FIG. 3.

The mechanism by which diffusion is achieved may be explained on the basis of an activity or chemical potential gradient wherein the confined drug relieves its internal concentration by spreading out into the adjacent medium. As the drug is removed from the device and absorbed by eye tissues or carried away by the eye fluids, the diffusive action continues until the source of drug 21 has been substantially consumed. The drug will have a definite and characteristic rate of passage through the release rate controlling material of the insert. It is preferred, although not essential, that drug 21 essentially be depleted or consumed from the reservoir 20 before membrane material 22 completely bioerodes. However, if it is desired to obtain a zero order drug release rate over the active releasing period of the insert, prior depletion of drug is an essential requirement. Of course, it will be appreciated that the device of type shown in FIG. 3 makes possible drug-time patterns of release other than zero order. Another reason for the depletion of drug from matrix reservoir 20 prior to the complete erosion of membrane material 22 is to eliminate the possibility of the sudden release of drug from the reservoir to the eye at the time of total erosion of membrane 22, as a result of the high permeability of material 20 to drug, as hereinafter described. Therefore, membrane material 22 should be selected with regard to its erosion rate, thickness and permeability to drug 21 in respect to the amount of drug in core material 20. It will, of course, be appreciated that the inner core material 20 will not begin to erode until free to contact eye fluids, which time will be subsequent to the substantially complete erosion of outer membrane 22.

The reservoir 20 primarily functions as a depot for the drug rather than as a rate control barrier. Therefore, it should be highly permeable to passage of drug by diffusion. In contrast, membrane 22 which acts as the rate-limiting barrier to control drug release must be only slowly permeable to the passage of drug, with the exact value determined by the desired release rate. Thus, it is important to the successful practice of this invention that the membrane 22 have a lower permeability to the drug by diffusion than does the matrix material 20. The initial ratio of permeability rates for drug for the matrix material 20 to membrane material 22 should be approximately between 10:1 and 100:1, and preferably between 2:1 and 10:1. It will be noted that the effective drug release rate through the membrane 22 may tend to increase somewhat in the case wherein membrane erodes from its surface, and the effective release rate through the membrane material 22 will tend to decrease somewhat as the concentration of drug in the reservoir 20 depletes. These opposite effects tend to compensate each other to a large degree so as to give an overall uniform rate throughout most of the drug release period. However, in cases where the release rate of the device is not overly sensitive to changes in thickness in the membrane material, or where the change in thickness of the membrane material are small during the drug releasing period, it is preferred, in order to obtain zero order drug release, that the drug be sparingly soluble in the reservoir matrix material so as to retain substantially the same thermodynamic activity of the drug throughout the release period. By "sparingly soluble" is meant that the fractional amount of drug dissolved in the reservoir material should be in range of from 0.1% to 35% by weight of the total amount of drug to be delivered, such that solid particles of drug are present throughout most of the drug release period. Moreover, for best results, the rate of passage of drug through membrane 22 should not exceed the rate of removal or clearance of drug from the exterior of the membrane by eye tissues. This insures that the drug delivery rate is controlled by diffusion through the membrane 22, which can be controlled.

As disclosed above, the selection of appropriate materials for fabricating the ocular inserts will be dependent upon their erosion rates in the eye. The erosion rate of outer membrane material 22 in the eye is determined by the desired ophthalmic dosage regimen, as well as the length of time the device is to remain in the eye. Under optimum conditions, the erosion rate should be such that substantially all of the membrane material 22 bioerodes in the eye tissue soon after the drug has been substantially depleted from the reservoir 20, preferably no later than in a period of from 24 hours thereafter, if possible.

The erosion rate of inner core material 20 can be the same as, greater than, or less than the erosion rate of outer membrane material 22, although it is preferred that it be greater. The preference of the higher erosion rate for the inner matrix material 20 is predicated on the fact that the primary function of this material is to serve as a reservoir for the drug 21. Erosion of this material does not commence until the drug 21 contained therein has been substantially depleted and the erosion of outer layer 22 essentially completed. At this stage, no purpose is served by further retention of core material 20 in the eye. It is preferred that the erosion rate for core material 20 is such that all of the material bioerodes in the eye tissue in a relatively quick period of time, preferably within 8 hours after the substantially complete erosion of the outer membrane 22 has taken place.

It will of course be appreciated that correlation of the optimum desired material erosion rate and the drug release rate for a given membrane material 22 may in some cases be difficult under certain design conditions. In these cases, selection of a material having the desired optimum drug release rate should be made with the proviso that the erosion rate be slow enough to ensure that the membrane layer 22 does not totally erode prior to the depletion of drug from core material 20. If this procedure is followed, there will be a period of time in which the ocular insert remains in the eye but dispenses no drug. This, however, is not of serious consequence, as a fresh ocular device can be inserted concurrent with the final stages of the erosion of the original drug depleted device.

The thickness of the inner core 20 can vary, consistent with dimensions resulting in comfortable retention of the device in the eye and physical capability to incorporate the desired amount of drug. The thickness of outer membrane 22 can also vary, depending upon overall comfortable retention of the device in the eye, as well as providing the desired drug release rates and a sufficient mass of material so as to enable the substantially complete depletion of drug from core 20 prior to the complete erosion of the layer 22, thereby insuring, if desired, that drug 21 is advantageously released from the insert in a zero order manner as heretofore discussed.

In general, to design a device of the type shown in FIG. 3 it is first necessary to select the drug to be used, its dosage, and the period of therapy. This establishes the required drug release rate and amount of drug to be incorporated in the device. Materials for both the reservoir and rate controlling membrane which have the appropriate permeability characteristic and erosion rates can then be correlated with thickness and effective surface release area to fabricate a device which meters the desired amount of drug to the eye over the established period of time and thereafter completely erodes in the eye.

FIG. 4 illustrates generally, by reference numeral 30, another bioerodible ocular insert of this invention having a hollow interior reservoir 32 containing drug formulation 21 in the reservoir 32. Rate controlling bioerodible membrane 22 surrounds the reservoir 32 and controls the flow of drug from the reservoir 32 to the eye. This embodiment differs from that illustrated in FIG. 3, mainly in that therein the reservoir 20 is formed of a matrix material with the drug dispersed therethrough, whereas in the embodiment of FIG. 4 the drug 21 is confined in the hollow reservoir container 32. Alternatively (not shown), the drug contained within the hollow reservoir 32 can be surrounded with an additional layer of material to facilitate the handling of drug during fabrication. This material should be highly permeable to drug in contrast to rate controlling membrane 22. The insert shown in FIG. 4 operates in a manner similar to the device illustrated in FIG. 3, as described above. It is imperative that the drug 21 be depleted from the reservoir 32 prior to the complete erosion of rate controlling membrane 22 in order to avoid a sudden and unwanted release of drug from the reservoir 32 to the eye.

Another aspect of the invention resides in an ocular insert for the controlled continuous administration of a predetermined dosage of drug to the eye over a prolonged period of time, comprising a body of bioerodible drug release rate controlling material containing a drug formulation confined therein, the body being of an initial shape which is adapted for insertion and retention in the sac of the eye bounded by the surfaces of the bulbar conjunctiva of the sclera of the eyeball and the palpebral conjunctiva of the lid, the body continuously metering the flow of a therapeutically effective amount of drug to the eye at a controlled rate over a prolonged period of time, and wherein the body bioerodes in the environment of the eye concurrently with the dispensing or at a point in time after the dispensing of the therapeutically desired amount of drug. FIG. 5 illustrates one embodiment of the above described ocular insert, wherein the device 50 is comprised of a body of microporous, solid or gel bioerodible drug release rate controlling matrix material 51 having drug 21 dispersed therethrough. The matrix material 51 functions both as a drug reservoir source and rate release controlling material to continuously dispense a metered amount of drug to the eye and surrounding tissues over a prolonged period of time through the hereinabove discussed primary drug transfer mechanisms of:

1. Permeation Control Release, and/or
2. Erosion Control Release The actual control mechanism is dependent upon the design of the insert with particular regard to the combination selection of drug and release rate controlling material. The following are generalized considerations to be made in order to properly design an ocular insert with particular regard to the administration of drugs which are water soluble.

"Water soluble" is defined to mean materials which are soluble in water to a degree which exceeds approximately 50 parts per million.

In cases where the drug to be released is not water soluble, or in cases where the drug is water soluble and the drug release rate controlling material is substantially water impermeable, (hydrophobic), satisfactory devices can be made with the actual drug release from the device to the eye being effected by either of the transfer mechanisms, or a combination of the transfer mechanisms, (1) and (2) above. The actual mode of drug transfer will depend upon such factors as whether the drug release rate controlling material is of a hydrophobic or hydrophilic nature, whether the drug is soluble or insoluble in the rate controlling material, and on the erosion pattern of the rate controlling material, e.g. surface erosion or otherwise. However, it has been found that it is not preferred to deliver water soluble drugs using highly water permeable release rate controlling matrix materials, e.g. hydrophilic materials, over prolonged periods of time because the rate of release of drug is governed by that of simple dissolution of the drug in tear fluid. It is therefore preferred in these cases that certain modifications be made to insolubilize the drug. Insolubilization of the drug can be accomplished in a number of ways, among which include the forming of pharmaceutically acceptable derivatives of the drug which are not water soluble. These derivatives can be prepared by art known techniques and then used in the practice of the invention. Of course, the drug derivative should be such as to convert to the active drug within the body through the action of body enzymes, assisted transformations, pH, specific organ activities, and the like. Alternatively, insolubilization of the drug can be effected by coating the drug, such as by microencapsulating the drug, with a material to decrease the rate of release of drug by simple dissolution in tear fluid. Therefore, devices of the type illustrated in FIG. 5 are preferrably made, in cases where the drug is water soluble and the rate controlling matrix material is water permeable, by insolubilizing the drug.

Methods and materials for microencapsulating the drug in order to decrease the drug solubility in water are described hereinafter with regard to the reservoirs in FIG. 6. These microencapsulating methods, structures and materials are suitable for the drug encapsulation in the embodiment of the type illustrated in FIG. 5, with the qualification that in FIG. 5 the microcapsule material does not provide the release rate controlling step from the device as it does in the device illustrated in FIG. 6.

Figure 6:
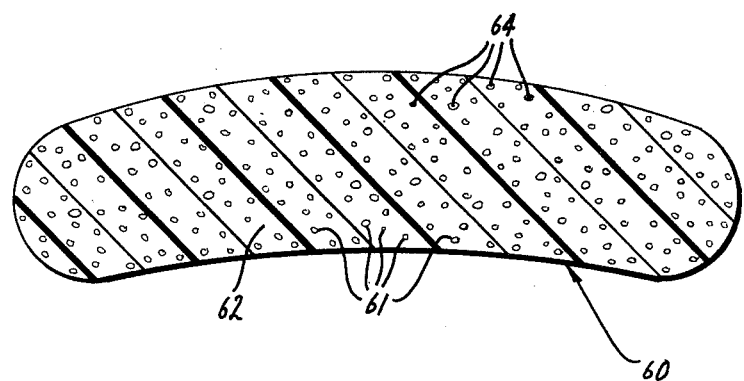
Figure 7:
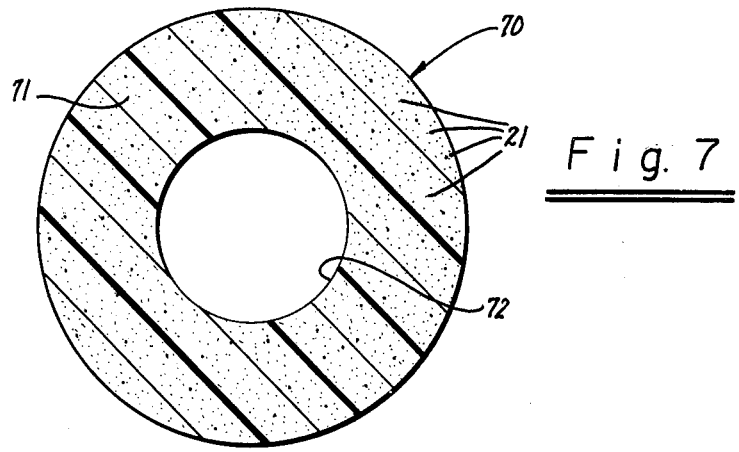

In still another aspect, as illustrated in FIG. 6, this invention resides in an ocular insert for the controlled continuous administration of a predetermined dosage of drug to the eye over a prolonged period of time, comprising a plurality of reservoirs, each of the reservoirs comprised of a drug formulation confined within a drug release rate controlling material, the reservoir characterized by being either:

1. a microcapsule of initial size and configuration such as to be capable of being eliminated from the ocular cavity through the punctum with tear fluid, or
2. a microcapsule of bioerodible material; the reservoirs being distributed throughout a bioerodible matrix material permeable to the passage of drug at a higher rate than through said drug release rate controlling material, the latter material metering a therapeutically effective amount of drug from the reservoir to the eye at a controlled rate over a prolonged period of time, the insert being of an initial shape which is adapted for insertion and retention in the sac of the eye bounded by the surfaces of the bulbar conjunctiva of the sclera of the eyeball and the palpebral conjunctiva of the lid, and wherein the reservoir and matrix are eliminated from the ocular cavity by bioeroding in the environment of the eye or the reservoir eliminated by passage through the punctum, the elimination taking place concurrently with the dispensing or at a point in time after the dispensing of the therapeutically desired amount of drug.

FIG. 6 illustrates an ocular insert 60 of this invention, particularly suited for administering a water soluble drug 64. The drug delivery device 60 is comprised of a bioerodible matrix 62 having dispersed therethrough a plurality of reservoirs 61. The reservoirs 61 are microcapsules comprised of a drug whether in solid form, liquid form or in admixture with a carrier, confined within a drug release rate controlling material. Drug molecules released from the reservoirs 61 pass into the matrix 62 and then migrate through the matrix 62 for administration of drug to the eye. Release of drug from the reservoir is the rate controlling step for release of drug from the device. In construction, the device can be viewed as a single unit device comprising two structures acting in concert for effective drug administration to the eye. One structure pertains to the reservoirs 61 which are microcapsules comprising a microbody of drug release rate controlling material having drug 64 confined therein, and the other structure relates to the bioerodible matrix 62 housing the reservoirs and is formed of a material permeable to the passage of drug.

The reservoirs 61 can be formed as a hollow container having a drug therein formed from drug release rate controlling material. Additionally, the reservoir 61 can be a solid particle having a drug distributed therethrough and formed of a drug release rate controlling material. Alternatively, the reservoir 61 can be a porous structure formed of a material possessing drug release rate controlling properties. Reservoir 61 can have the conventional aggregate structure and particulate structure of conventional geometric shape. By controlling the structure of the reservoirs of the drug delivery device, the invention makes possible a drug time pattern of release, including a zero order drug release. Thus, in the presently preferred embodiments for obtaining a zero order release, the reservoir is formed as a capsule containing the drug therein and surrounded by a rate controlling membrane, or the reservoir is a solid matrix with a limited number of discrete particles of drug contained therein. Other patterns of release can be obtained, e.g. sinusoidal, parabolic and the like by the appropriate selection of reservoirs having different release rates which are then dispersed in a given matrix.

The materials suitable for fabricating the reservoir 61, whether of hollow, solid, porous, semi-porous or the like structures, are generally those materials capable of forming membranes with or without pores or voids, or coatings through which the drug can pass at a controlled rate by the process of diffusion. Suitable materials for forming the reservoirs are naturallyoccurring or synthetic materials that are non-toxic and which preferably have a low solubility and/or low diffusivity to water. In general, these qualities will be possessed by rate release controlling materials that are hydrophobic in nature. The rate controlling materials used for the reservoir 61 can be bioerodible and alternatively, when the reservoir 61 is of an initial size and configuration such as to be capable of being eliminated from the ocular cavity through the punctum with tear fluid can be made of non-bioerodible material. Microcapsules, preferably of approximately 100 micron size or less, will be of suitable dimension for proper punctum passage.

Exemplary non-bioerodible materials suitable for fabricating the microcapsules when of an initial size such as to pass through the punctum are drug release rate controlling materials such as hydrophobic polymers, e.b. polyvinylchloride, nylon, silicone rubber, cholesterol; substituted alkyl celluloses such as hydroxypropyl methyl cellulose, methyl cellulose, ethyl cellulose, cellulose acetate; waxes, e.g. paraffin, ethylene wax, hydrogenated castor oil; $C_{10}$ to $C_{20}$ fatty acids, e.g. stearic acid, palmitic acid; hydrophilic polymers, e.g. polymerized esters of methacrylic acid (Hydron), and the like. Bioerodible materials suitable for preparing the microcapsule reservoirs are disclosed hereinafter. The actual material selected for fabricating the microcapsule reservoir is one that can slow down the rate of release of the water soluble drug to the desired level. Preferred are the hydrophobic materials. Although hydrophilic type materials can sometimes be employed for fabricating the reservoir in cases where the water soluble drug is not too highly permeable therein, in most cases thicker coatings of microcapsule material and larger microcapsule diameters will be required than for hydrophobic type microcapsule materials, as explained immediately hereinafter.

Among other factors which must be considered, in addition to the nature of the reservoir rate controlling material, and which affect the rate of release of drug from the microcapsule, are the microcapsule size, the density of drug and the thickness of the reservoir wall. Qualitative guides in this regard are that the rate of release of drug will decrease with corresponding increasing values for each of these parameters. A typical combination of drug and coating is a 100 micron chloramphenicol particle coated with polylactic acid to a thickness of 3 microns with the microcapsule being dispersed in a cross-linked gelatin matrix.

Additionally, if desired, particles of a known drug carrier, such as starch, gum acacia, charcoal, gum tragacanth, calcium carbonate, polyvinylchloride, and the like, can be impregnated with the drug and encapsulated with another material such as the encapsulating materials previously discussed which function as a membrane to meter the flow of drug to the matrix.

Any of the standard encapsulation or impregnation techniques known in the art can be used to prepare the microcapsules 61 to be incorporated into the matrix material 62 in accord with this invention. Thus, the drug, a mixture of drug, or drug solution can be added to the encapsulating material in liquid form and uniformly distributed therethrough by mixing; or solid encapsulating material can be impregnated with the drug by immersion in a bath of the drug to cause the drug to diffuse into the material. Subsequently, the solid material can be reduced to fine microcapsules by grinding, each of the microcapsules comprising drug coated with and distributed throughout the encapsulating material. Alternatively, fine particles or solutions of the drug can be encapsulated with a coating. One suitable technique comprises suspending dry particles of the drug in an air stream and contacting that stream with a stream containing the encapsulating material that coats the drug with a membrane permeable to drug.

Another standard method of microencapsulation suitable for the purpose of the invention is the coacervation technique. The coacervation technique of fabrication as conventionally employed consists essentially of the formation of three immiscible phases, a liquid manufacturing phase, a core material phase and a coating phase with deposition of the liquid polymer coating on the core material and rigidizing the coating, usually by thermal, cross-linking or desolvation techniques to form microcapsules. Techniques for preparing microcapsules, such as the classic Bungenberg de Jong and Kaas method are reported in Biochem. Z, Vol. 232, pp. 338–345, 1931; Colloid Science, Vol. 11, "Reversible System", edited by H. R. Kruyt, 1949, Elsevier Publishing Company, Inc., New York; J. Pharm. Sci., Vol. 59, No. 10, (1970), pp. 1367–1376; and, Remington's Pharmaceutical Science, Vo. XIV, Mack Publishing Company, Easton, Pa., 1970, pp. 1676–1677. Other procedures for preparing micro-capsules are set forth in West German Patent No. DT-1939–066; and the like.

Materials suitable for use as the matrix material 62 in the device of the type illustrated in FIG. 6 must be bioerodible and permeable to passage of drug at a rate which is greater than the permeation of drug through the reservoir material. Therefore, it is not necessary for the matrix material 62 to have drug release rate controlling properties. The bioerosion rate of matrix material 62 can be such that the material bioerodes concurrently with the dispensing of the drug from the reservoir 61 or at a point in time after the dispensing of the desired amount of drug from the reservoir. It is preferred, however, although not critical to the successful practice of the invention, that the bioerosion pattern and rate of the matrix material be such that the drug be substantially depleted from the reservoir 61 prior to the release of the reservoir from entrapment within the matrix material 62 and elimination by bioerosion or by passage through the punctum. This is predicated on the fact that the primary function of the matrix material is to serve as a carrier or housing for the reservoir 61. The matrix material can be of a water permeable or water impermeable nature although when the drug is water soluble, the impermeable materials are preferred.

Although the device of the type illustrated in FIG. 6 is particularly well suited to the administration of water soluble and so described above, it will be appreciated that it is equally well adapted to the administration of drugs as hereinafter set forth which are not water soluble and with each or both the reservoir and matrix also being formed from substantially water permeable or water impermeable materials.

Devices of the type shown in FIGS. 5 and 6 can be designed by first selecting the drug to be used, its dosage, and the period of therapy. This establishes the required drug release rate and amount of drug to be incorporated in the device. Materials having the appropriate drug release rate characteristics and erosion rates can then be correlated with the effective surface release area to fabricate a device which meters the desired rate of the drug to the eye over the established period of time. A particular added advantage of a device of the type as illustrated in FIG. 6 is the fact that the number of reservoirs employed can be varied in order to achieve the desired drug release rate from the device.

FIG. 7 illustrates a donut-shaped outline of an ocular insert 70 of this invention. The insert is comprised of a hollow center portion 72 which fits over the corneal portion 5 of the eye with the body of bioerodible drug rate release controlling matrix material 71 resting on the scleral surface 4 and having drug 21 dispersed therein. The hollow central portion 72 should be of a size such that the matrix material 71 does not touch the corneal area of the eye which is sensitive to pain and obstructs the vision of the patient. In order to facilitate insertion of the ocular device in the eye, the matrix material 71 can be concentrically affixed to the outer extremity of a contact lens by means of any of the well known dermatologically acceptable pressure-sensitive adhesives, such as the esters of acrylic and methacrylic acid with lower alkyl alcohols, e.g. n-butanol, 2-methyl pentanol, and the like. Insertion of the device in the eye can then be made by using any of the well known tools commonly employed to insert contact lenses. In operation, this device functions in a manner similar to that described in FIG. 5.

Any of the drugs used to treat the eye and surrounding tissues can be incorporated in the ocular insert of this invention. Also, it is practical to use the eye and surrounding tissues as a point of entry for systemic drugs or antigens that ultimately enter circulation in the blood stream, or enter the naso-pharyngeal area by normal routes, and produce a pharmacologic response at a site remote from the point of application of the ocular insert. Thus, drugs or antigens which will pass through the eye or the tissue surrounding the eye to the blood stream or to the nasal-pharyngeal, esophageal or gastrointestinal areas, but which are not used in therapy of the eye itself, can be incorporated in the ocular insert.

Suitable drugs for use in therapy of the eye with the ocular insert of this invention consistent with their known dosages and uses are without limitation: antibiotics such as tetracycline, chlortetracycline, bacitracin, neomycin, polymyxin, gramicidin, oxytetracycline, chloramphenicol, gentamycin, and erythromycin; antibacterials such as sulfonamides, sulfacetamide, sulfamethizole and sulfisoxazole, antivirals, including idoxuridine; and other antibacterial agents such as nitrofurazone and sodium propionate; antiallergenics such as antazoline, methapyriline, chlorpheniramine, pyrilamine and prophenpyridamine; anti-inflammatories such as hydrocortisone, hydrocortisone acetate, dexamethasone, dexamethasone 21-phosphate, fluocinolone, medrysone, prednisolone, methylprednisolone, prednisolone 21-phosphate, prednisolone acetate, fluoromethalone, betamethasone and triamcinolone; decongestants such as phenylephrine, naphazoline, and tetrahydroazoline; miotics and anticholinesterases such as pilocarpine, eserine salicylate, carbachol, di-isopropyl fluorophosphate, phospholine iodide, and demecarium bromide; mydriatics such as atropine sulfate, cyclopentolate, homatropine, scopolamine, tropicamide, eucatropine, and hydroxyamphetamine; and sympathomimetics such as epinephrine.

Drugs can be in various forms, such as unchanged molecules, components of molecular complexes, or nonirritating, pharmacologically acceptable salts such as hydrochloride, hydrobromide, sulfate, phosphate, nitrate, borate, acetate, maleate, tartrate, salicylate, etc. For acidic drugs, salts of metals, amines, or organic cations (e.g. quaternary ammonium) can be employed. Furthermore, simple derivatives of the drugs such as ethers, esters, amides, etc. which have desirable retention, release or solubility characteristics, but which are easily hydrolized by body pH, enzymes, etc., can be employed. The amount of drug incorporated in the ocular insert varies widely depending on the particular drug, the desired therapeutic effect, and the time span for which the ocular insert will be used.

The above drugs and other drugs can be present in the reservoir alone or in combination form with pharmaceutical carriers. The pharmaceutical carriers acceptable for the purpose of this invention are the art-known carriers that do not adversely affect the drug, the host, or the material comprising the drug delivery device. Suitable pharmaceutical carriers include sterile water; saline; dextrose; dextrose in water or saline; condensation products of castor oil and ethylene oxide combining about 30 to about 35 moles of ethylene oxide per mole of castor oil; liquid glyceryl triester of a lower molecular weight fatty acid; lower alkanols; oils such as corn oil; peanut oil; sesame oil, and the like, with emulsifiers such as mono- or di-glyceride of a fatty acid, or a phosphatide, e.g. lecithin, and the like; glycols; polyalkylene glycols; aqueous media in the presence of a suspending agent, for example, sodium carboxymethylcellulose; sodium alginate; poly(vinylpyrrolidone); and the like, alone, or with suitable dispensing agents such as lecithin; polyoxyethylene stearate; and the like. The carrier may also contain adjuvants such as preserving, stabilizing, wetting, emulsifying agents, and the like.

To provide compatibility with the eye and surrounding tissues, at least for the initial period after insertion, the surface of the ocular insert in contact with the eye can be coated with a thin layer, e.g. from 1 to 2 microns thick, bioerodible hydrophilic material. Exemplary of the suitable materials for this purpose are the water soluble hydrophilic polymers of uncross-linked hydroxyalkyl acrylates and methacrylates, as disclosed in U.S.

Pat. No. 3,576,760, e.g. Hydron-S, gelatin, polysaccharides, e.g. agar, gum arabic, and the like.

The ocular insert is intended to provide a complete dosage regimen for eye therapy over this prolonged period. Therefore, the amount of drug to be incorporated in the device is determined by the fact that sufficient amounts of drug must be present to maintain the desired dosage level over the therapeutic treatment period. Typically, from 1 microgram to 1 gram or larger of drug is incorporated in the ocular insert, the exact amount of course depending upon the drug used and treatment period. Illustratively, in order to treat glaucoma in an adult human, the daily release dosage should be in the range of between 25 micrograms to 1000 micrograms of pilocarpine per day. Thus, for example, using pilocarpine with a device intended to remain in place for 7 days, and with a release rate of 500 micrograms of drug per day, 3.5 milligrams of pilocarpine will be incorporated in the device. Other devices containing different amounts of drug for use for different time periods and releasing drug at higher or lower controlled rates are also readily made by the invention.

Further, in practicing this invention one can employ any of the aforementioned listed drugs, consistent with their known dosages and uses, to establish a release rate, e.g. micrograms/insert/day. Exemplary of the dosages to be used are:

| | |
|---|---|
| Antibiotics, such as polymixin: | 250 micrograms/insert/day |
| Sulfonamides, such as sulfacetamide: | 500 micrograms/insert/day |
| Antivirals, such as idoxuridine: | 5 micrograms/insert/day |
| Anti-inflammatories, such as hydrocortisone acetate or prednisolone: | 500 micrograms/insert/day |

Materials which are generally suitable for use as the bioerodible drug release rate controlling microcapsules, membrane and matrix materials of the ocular inserts of this invention and for the bioerodible inner reservoir 20 in FIG. 3 and matrix 62 in FIG. 6 are those materials which are non-toxic and compatible with the drug used, with the particular selection being made consistent with earlier comments made regarding desired erosion and release rates. Exemplary of the materials which can be employed for these structures are:

1. -Polyanhydrides

Hydrolytically biodegradable polyanhydride polymers of the general formula:

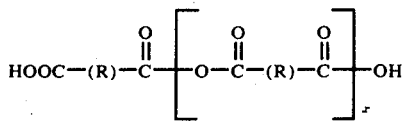
    I which are the reaction products obtained by polymerization of aliphatic or aromatic monomeric dibasi acids of the formula:

HOOC-R-COOH          II or the anhydrides or mixtures of these acids wherein:
R is a radical of the formula —T— or —Y—;

Y is a radical containing mono or dinuclear arylene group such as phenylene; substituted phenylene, e.g. hydroxy phenylene, $C_1$—$C_7$ alkyl phenylene, $C_1$—$C_7$ alkoxy phenylene, bis-(phenoxy) $C_1$-$C_7$alkylenes; and the like;

X has a value such that the molecular weight of the polymer is preferably not greater than 50,000, although higher values can be employed;

T is an aliphatic alkylene or alkylene ether radical containing from 2 to 14 carbons and preferably from 4 to 10 carbons in the backbone chain, optionally with a minor amount of branching, such as methylene, ethylene, propylene, hexylene, 2methyl-propylene, 4 ethyltetradecylene, and the like.

Among the representative monomers can be included adipic acid, pimelic acid, suberic acid, azelaic acid, sebacic acid, succinic acid, glutaric acid, trimesic acid, etc.

These polyanhydrides (1) are known materials and can be conveniently prepared by condensing the corresponding dibasic acid or anhydride in the presence of $SOCl_2$, benzene and a lower alkyl ester of acetic acid such as ethyl acetate. Alternatively, the desired dibasic acid or anhydride thereof can be mixed with acetic anhydride to form a mixed anhydride which, on further heating, yields the desired polymeric anhydride. Further description of methods for the preparation of these materials can be found in U.S. Pats. No. 2,073,799, 2,668,162, 2,676,945; and Introduction to Polymer Chemistry, Stille, Wiley Publishing Co. (1962). The polyanhydride polymers (1) per se, their preparation as exemplified, and use form no part of the present invention.

2. - Polyesters

Polyesters of the general formula:

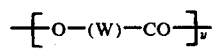
    III and mixtures thereof, wherein:
W is a radical of the formula —$CH_2$—; or

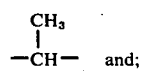 and;

y has a value such that the molecular weight of the polymer is from about 4,000 to 100,000.

These polymers are polymerization condensation products of monobasic hydroxy acids of the formula:
   $C_nH_{2n}(OH)COOH$          IV wherein *n* has a value of 1 or 2 especially lactic acid and glycolic acid. Also included are copolymers derived from mixtures of these acids. The preparation of polymers of the formula III per se, forms no part of the present invention and several procedures are available and reported by Filachione, et al, Industrial and Engineering Chemistry, Vol. 36, No. 3, pp. 223–228, (March 1944; Tsuruta, et al. Macromol. Chem., Vol. 75, pp. 211–214 (1964), and in Unites States Pat. Nos. 2,703,316; 2,668,162; 3,297,033; and 2,676,945.

3. - Cross-Linked Anionic Polyelectrolytes

Membrane and matrix structures comprising cross-linked substantially water insoluble polymeric coordination complexes. These products can be made by several alternative procedures.

Method A comprises the sequential steps of:
a. preparing an aqueous solution containing an initially water soluble anionic polyelectrolyte, and adding thereto a polyvalent metal cation capable of coreacting therewith to form a water insoluble cross-linked precipitate;
b. adding to said mixture a sufficient amount of complexing reagent in the form of an electron donor molecule to render the reaction product water soluble by forming a coordination complex with the reactants;
c. fabricating the solution into the desired membrane shape; and then
d. substantially removing the electron donor molecule from the system to cross-link the polyelectrolyte and recovering the thus prepared solid shaped structures.

Alternatively, the complexing reagent can be added to the solution of anionic polyelectrolyte prior to the addition of the polyvalent cation to maintain the reaction product in solution in lieu of resolubilizing the precipitate.

Method B comprises the sequential steps of:
a. fabricating a solution of an initially water soluble plasticized anionic polyelectrolyte into the desired shape;
b. dipping the thus formed shape into an aqueous solution of a polyvalent metal cation to cross-link the anionic polyelectrolyte; and
c. recovering the thus prepared water insoluble cross-linked structure.

This material, methods for its preparation, and the use thereof, is the sole invention of Alan S. Michaels. It is more fully described and claimed in copending application Ser. No. 248,168 (internal Docket No. Pm 5015) owned by the assignee of this invention, filed on April 27, 1972, now U.S. Pat. No. 3,867,519 and generally described below.

Structures prepared from polymeric compositions of the above type are characterized by their ability to advantageously control the release rate of drug through the material. When placed in contact with body fluids, e.g. tears, such polymeric structures sorb the tear fluid and swell by hydration to an extent governed by the degree of cross-linking as determined by the polyvalent metal cation content and character. As previously discusssed, control of drug release rate by a Permeation Control Release mechanism by means of swellable microporous hydrophilic materials is advantageous. This is so, since the release rate is dependent on the degree of swelling of the structure which can be controlled over a wide range.

Among the anionic polyelectrolyte polymers which may be interacted to produce the cross-linked structures which are useful in the present invention are those which are soluble in eye fluids and have a sufficiently high molecular weight, typically at least 10,000, to be solid and capable of film formation, and containing a plurality of functional groups which are reactive with the polyvalent metal cation to form a salt therewith. Preferably, the functional group is an alkali metal or ammonium salt of a carboxylate, sulfate, sulfonate or phosphate. These functional groups can be characterized as being dissociable anionic groups which are chemically bonded to the polymeric chain. Exemplary of these polymers are: polysaccharides, e.g. K-carrageenin, pectinic acid, heparin sulfate, hyaluronic acid, heparin, natural gums such as algin, locust bean gum, agar, pectin, gum arabic, gum tragacanth; modified natural and synthetic polymers such as carboxymethylcellulose, carboxymethyl starch, polystyrene sulfonic acid, polyvinyl sulfuric acid, poly(vinyl sulfonic acid), polyvinyl methylol sulfonic acid, hydrolyzed poly(vinyl acetate/maleic anhydride), polyvinyl ether-maelic anhydride, poly(ethylene-maleic anhydride), poly(acrylic acid), poly(methacrylic acid) and copolymers thereof with acrylic or methacrylic esters, poly(vinyl acetate), poly(vinyl alcohol), poly(vinyl chloride), styrene, and other materials of the same general type.

Preferred are the naturally occurring vegetable-derived water soluble polysaccharide polymers which are essentially devoid of animal or human toxicity, and which decompose in the body into simple sugars.

The polyvalent metal cations which are interacted with the initially water soluble anionic polyelectrolytes include di, tri or tetra valent metals such as copper, mercury, chromium, nickel, zinc, cobalt, ferric and ferrous iron, aluminum, tin, bismuth, calcium, magnesium, and the like. It is to be understood that any polyvalent metal can be employed which is capable of coreacting with the polyelectrolyte to form a water insoluble precipitate and which is innocuous in the body. The anion associated with the metal cation is preferably a halide, e.g. chloride; or sulfate, nitrate, although any innocuous ion can be used.

The complexing reagents employed in Method A are any of those materials which are capable of solubilizing or maintaining the polyelectrolytepolyvalent cationic reaction product in solution so as to enable fabrication of the solution into the desired shape. Exemplary of these materials are primary, secondary and tertiary amines such as mono, di, or trimethyl amine, mono, di, or tri-ethanolamine, morpholine, pyridine, piperidine, piperazine, aniline, 2-methyl imidazole, ethylene diamine and higher polyethylene polyamines, and ammonia.

The complexing reagent must be present in solution in an amount sufficient to prevent precipitation of the reactive components. This amount will usually be about 5% by weight of the total solution, preferably at least 0.5% by weight. Although amounts as great as 50% or more weight of the total solution may be used, it is unnecessary and frequently undesirable to employ any more than the minimum required to prevnt precipitation of the polyelectrolytes. In general, the concentration of the polyelectrolyte must be at least 0.5% by weight and preferably above 1% by weight of the mixture in order to obtain continuous solids in the subsequent processing. Molar ratios of anionic polyelectrolyte to polyvalent metal of from 1 to 10, and preferably from 2 to 5, are satisfactory. The solution thus prepared is then caused to gel by changing conditions so as to permit precipitation to occur by breaking down the coordinate complex so as to cross-link the polymer with metal. Gelation of the polymeric complex solute can be effected by reducing the effective concentration of the complexing reagent by neutralization thereof with acid, or removal in the case of volatile reagents by evaporation in the presence of heated moist air. The structure can be obtained by the usual process of casting, extruding the mixture, or coating onto a suitable substrate and then drying the formed object by suitable means.

In both Method A and Method B, the plasticizer, when included, is preferably added to the structure when fabricating the solution into the desired shape. Suitable plasticizers are described hereinafter.

The degree of cross-linking of the polymer by the metal ion can be controlled by adjusting the ratio of metal to polymer in the initial solution, thereby producing materials of varying hydrophilicities. When placed in contact with a body fluid such as tears, these polymeric structures biodegrade by virtue of the gradual extraction and chelation of the polyvalent ion by endogenous proteins, polysaccharides, and other substances present in these fluids. By varying the degree of cross-linking, the rate of drug release and biodegration can be varied over wide limits. If a natural gum (e.g. algin) is used in the formulation, after dissolution, enzymatic hydrolytic processes will cleave the solubilized polymer into innocuous sugars which are absorbed into the eye and surrounding tissues.

4. - Cross-Linked Gelatin

Gelatin is obtained by the selective hydrolysis of collagen by means well known to those skilled in the art and comprises a complex mixture of water soluble proteins of high molecular weight. As used herein, the term cross-linked gelatin means the reaction product of gelatin or a gelatin derivative with a cross-linking agent reactive with either the hydroxyl, carboxyl or amino functional groups of the gelatin molecule and substantially unreactive with the peptide linkage of the gelatin molecule, the product of reaction having an average molecular weight preferably of from 20 to 50,000 between cross-links, although higher values can be employed, and which product is biodegradable in the environment of the eye over a prolonged period of time.

Cross-linked gelatin materials are well known to those skilled in the art and can be prepared by reacting the cross-linking agent with gelatin under suitable reaction conditions. The degree to which the gelatin is cross-linked is dependent upon the processing conditions employed to carry out the reaction and markedly affects its characteristics with regard to the time required in order for the material to biodegrade in the eye. The rate and, therefore, the degree of cross-linking of the gelatin is primarily determined by: (1) the effective concentration of reactive groups present; (2) reaction time; (3) temperature at which the reaction is carried out; and (4) pH of the reaction environment. The choice of the particular conditions will of course depend on the properties desired for the end product as hereinafter discussed.

Exemplary of suitable cross-linking agents are: aldehydes, such as monoaldehydes, e.g. $C_1$–$C_4$ aldehydes, e.g. propanal, acetaldehyde, formaldehyde, acrolein, crotonaldehyde, 2-hydroxy adipaldehyde; dialdehydes, such as glutaraldehyde, glyoxal; other aldehydes such as starch dialdehyde, paraldehyde, furfural and aldehyde bisulfite addition compounds such as formaldehyde bisulfite; aldehyde sugars, e.g. glucose, lactose, maltose, and the like; ketones such as acetone; methylolated compounds such as dimethylol urea, trimethylol melamine; "blocked" methylolated compounds such as tetra(methoxymethyl) urea, melamine; and other reagents such as $C_1$–$C_4$ disubstituted carbodiimides; epoxides such as epichlorohydrin, Eponite 100 (Shell); para-benzene quinone; dicarboxylic acids, e.g. oxalic acid; disulfonic acids, e.g. m-benzene disulfonic acid; ions of polyvalent metals, e.g. chromium, iron, aluminum, zinc, copper; amines such as hexamethylene tetramine; and aqueous peroxydisulfate. See H. L. Needles, J. Polymer Science, Part A-1, 5 (1) 1 (1967).

Still another suitable method for cross-linking gelatin is that using irradiation; see for example Y. Tomoda and M. Tsuda, J. Poly. Sci., 54, 321 (1961).

The reactive groups present in gelatin, i.e. hydroxyl, carboxyl and amino functions are present per 100 grams of high quality gelatin in the following approximate amounts: 100, 75 and 50 meq of each of these groups, respectively. The number of reactive sites do not vary appreciably from one gelatin to another, i.e. Type A or B gelatins, unless major hydrolytic breakdown has occurred. These quantities may serve sa a general guide in determining the amount of cross-linking agent to be used. However, any discussion of the chemical reactions of gelatin must be made with regard to its very heterogeneous composition. Moreover, actual degradation rates are preferably determined experimentally as hereinafter exemplified in the Examples for a material prepared under a given set of conditions. For example, using formaldehyde as the cross-linking agent, concentrations thereof from 0.01% to 60% by weight, based on the weight of the gelatin in combination with reaction times of 0.1 hours to 5 days and at temperatures of from 4.0° C to 35° C will yield suitable products, the exact combination of concentration, temperature and time depending on the desired dissolution rate. General information on cross-linked gelatin can be found in Advances in Protein Chemistry, Vol. VI, Academic Press, 1951, "Cross Linkages in Protein chemistry", John Bjorksten.

5. - Other Bioerodible Materials

Other suitable materials which slowly bioerode in tear liquid may be classified as follows: (a) structural proteins and hydrocolloids of animal origin; (b) polysaccharides and other hydrocolloids of plant origin; and (c) synthetic polymers. Some of these matrix materials are suitable as in their native form but others, particularly hydrocolloids, require insolubilization either by chemical modification, or physical modification, such as orientation, radiation cross-linking, etc. Exemplary of the first category are: native and modified collagens, muscle proteins, elastin, keratin, resilin, fibrin, etc. Exemplary of polysaccharides and plant hydrocolloids are: algin, pectin, carrageenin, chitin, heparin, chondroitin sulfate, Agar-agar, Guar, locust bean gum, gum arabic, gum Karaya, tragacanth, gum Ghatti, starch, oxystarch, starch phosphate, carboxymethyl starch, sulfaethyl starch, aminoethyl starch, amido ethyl starch, starch esters such as starch maleate, succinate, benzoate and acetate, and mixtures of starch and gelatin; cellulose and its derivatives such as modified cellulosics, such as partially hydroxyethylated cotton obtained by the treatment of cotton with ethylene oxide or partially carboxymethylated cotton obtained by the treatment of cotton with caustic and choroacetic acid. Exemplary of synthetic polymers are: poly(vinyl alcohol), poly(ethylene oxide), poly(acrylamide), poly(vinyl pyrrolidone), poly(ethyleneimine), poly(acrylic acid) and poly(methacrylic acid) and copolymers thereof, poly(vinyl imidazole), poly(phosphate), synthetic polypeptides, polyvinyl alkyl ether, polyacryl-and polymethacrylamides, and copolymers of acrylamide and methacrylamide with up to 40% by weight of N-methylene bisacrylamide or N,N dimethylol urea; polyalkyl aldehydes, water soluble hydrophilic polymers of uncross-linked hydroxyalkyl acrylates and methacrylates, polyalkylene carbonates, and the like. The list is illustrative. Any bioerodible material which is compatible with the drug non-toxic and which has the desired erosion and release rates can be used. Preferred, however, are the anionic polyelectrolytes (3) and cross-linked gelatin (4).

As illustrated in FIG. 3, the inner core 20 of the ocular insert is made from a non-release rate controlling matrix material having the drug dispersed therethrough. Since the function of the inner core is to act as the reservoir for the drug, it is fabricated, in each case, of a material that provides the optimal environment and release characteristics for the drug being used. Materials suitable for forming the inner core are those which are compatible and highly permeable to the drug used and relatively rapidly bioerodible, exemplary of which are glycerinated gelatin, collagen, gum acacia, polyvinyl alcohol, polyvinyl pyrrolidone, alginic acid and alkali metal salts of alginic acid, starch phosphate, starch and gelatin, linear polyacrylamides and polymethacrylamides, and the like. In addition, any of the materials listed above under paragraphs number (1) to (5) can be employed for the matrix material 20 illustrated in FIG. 3, consistent with comments previously made for selection of this material as related to the outer release rate controlling membrane material 22.

Any of the materials listed under paragraphs number (1) to (5) can be employed for the matrix material 62 illustrated in FIG. 6 which houses the reservoirs 61, consistent with comments previously made for selection of this material as related to the release rate controlling reservoir material.

Drug can be incorporated in the ocular insert in many ways. When the ocular insert is in the form of a container, any of the encapsulation, bonding, and coating techniques and combinations thereof conventionally used in the art can be employed. When the ocular insert is a matrix with the drug dispersed therethrough, it can be fabricated by adding the drug to the monomers prior to polymerization; adding the drug to the polymer in liquid form, casting or molding and curing; or by impregnating the polymeric material, either before or after shaping to the form of the ocular insert, with the drug. When lamination is employed to fabricate the insert, the device may comprise a sheet of inner core material sandwiched between two sheets of outer layer material. To enhance adhesion between the layers, the inner core can be perforated or embossed. When the matrix material comprises a plurality of reservoir microcapsules they can be mixed with the matrix forming material, which can be in solid, semi-solid, or liquid form at the time of mixing, and then distributed therethrough by conventional methods, such as ball-milling, calendering, stirring, shaking, and the like. Where the reservoirs are generally compatible with monomers or prepolymers used to form the matrix, the reservoirs can be added at this earlier stage of formation, and the matrix formed in situ. The matrix material, however made and having the reservoirs distributed therethrough, can then be formed to a given drug design by molding, casting, pressing, extruding, drawing, rotational molding, compression and transfer molding, or like processes of manufacture. Also, depending on the material used to form the matrix, the monomers may be cured at this stage of manufacture. The ability to design and shape the matrix into highly reproducible shapes of controllable composition, readily results in fabrication of drug delivery devices with controlled characteristics. Other standard procedures, well known to those skilled in the art, can be used to fabricate the drug delivery devices of the invention.

The bioerodible release rate controlling material can have incorporated therein plasticizers, preservatives or other conventional additives employed in dosage forms. Exemplary plasticizers suitable for employment for the present purpose are the pharmaceutically acceptable plasticizers conventionally used, such as di-ethyl adipate, di-isobutyl adipate, di-n-hexyl adipate, di-isooctyl adipate, di-n-hexyl azelate, di-2-ethylhexylazelate, ethylene glycol dibenzoate, acetyl tri-n-butyl citrate, expoxidized soy bean oil, glycerol monoacetate, diethylene glycol dipelargonate, propylene glycol diluarate, iso-octyl palmitate, triphenyl phosphate, and the like. In addition, binding agents or disintegrating agents to regulate or to facilitate the bioerosion of the device can be employed. Exemplary of these materials are glycerin, dextrose, sorbitol, mannitol, sucrose, poly(ethylene glycol), monoglyceryl esters of fatty acids, methylcellulose, starch, and the like. The proportion of agent used will vary within broad limits depending upon the rate of disintegration desired, as well as upon the characteristics of the medicament involved. In general, about 0.01 parts to about 10 parts by weight for each part by weight of the medicament can be used, depending on the agent.

Enzymes can be incorporated into the release rate controlling material in order to further control the rate of bioerosion of the membrane or matrix materials of the device. Among the enzymes which can be included are pepsin, trypsin, ficin, papain, aminopeptidase, pectase, invertase, takadiastrase, pancreatin lactase, alpha amylase, beta amylase, and cellulase. Typical combinations of enzyme and material include: cellulase with cellulose and its derivatives; takadiastase with starch; aminopeptidase with polypeptides.

As previously discussed, devices of this invention are designed to dispense a metered amount of drug from the reservoir to the eye over a prolonged period of time, primarily through a Permeation or Erosion Control Release mechanism. Moreover, as heretofore indicated, in order to design these devices it is necessary to select materials having both the appropriate drug release rate characteristics and erosion rates. Those skilled in the art can readily determine the rate of permeability of drug through a material or selected combinations of polymeric materials. Standard methods of determining passage of drugs through drug permeable materials are exemplified in Encyl. Polymer Science and Technology, Vol. 5 and 9, pp. 65-85 and 795–807, 1968, and the reference cited therein; U.S. Pat. No. 3,279,996; Folkman and Edmonds, Circulation Research, 10:632, 1962; Folkman and Long, J. Surg. Res., 43:139, 1964; and Powers, J., Parasitology 51:53 (April 1965), No. 2 Section 2.

The erosion rate of a material can be determined by methods exemplified in the examples set forth hereinafter, or can be conducted with apparatus similar to the tablet disintegration apparatus described in U.S.P. XVII. Simulated tear fluid, e.g. saline fluid, is used in the test. The device is placed in the apparatus and initially contacted with simulated saline fluids for set periods of time. The weight loss of the device is then determined. The saline fluid is then removed and the course of the disintegration of the device is followed over the time course of the test by periodically determining the weight loss of the device or by measuring the amount dissolved by other suitable means, e.g. spectrophotometrically. The drug release rate is also determined in this test by periodically assaying the amount of drug that dissolves in these fluids over the course of the test.

It is intended that devices of this invention continuously dispense controlled amounts of drug to the eye over prolonged periods of time, that is, from periods ranging from 8 hours to 30 or more days. The material selected must therefore have an erosion rate in the eye, suitably modified if necessary, by the addition of additives, as hereinbefore mentioned, which is dependent upon the time period selected, as well as whether it is to be used as a rate controlling matrix of the type illustrated in FIGS. 5 or 7, or a rate controlling membrane of the type illustrated in FIGS. 3 and 4, or for the microcapsules of the type illustrated in FIG. 6, or a non-rate controlling material of the type illustrated in FIGS. 3 or 6, with regard to comments earlier made concerning the function of each of these materials. Generally, the following material erosion rates are satisfactory, with the exact rate selection dependent upon design considerations previously set forth:

| | Illustrative Erosion Milligrams/Day |
|---|---|
| Non-release Rate Controlling Matrix Material | 0.5 – 20 |
| Release Rate Controlling Membrane or Matrix Material | 0.1 – 15 |

From the foregoing, it is apparent that it is preferred to place the ocular device in the sac of the eye, either 7 or 11, bounded by the surfaces of the sclera of the eyeball and conjunctiva of the lid. The reason for this is the fact that obstruction with vision is avoided. Moreover, the scleral area of the eye is less sensitive to pain than are other portions of the eye. It is, however, contemplated herein that if desired, the device can be placed over the corneal portion 5 of the eye.

Insertion of the insert 12 into the eye can be satisfactorily accomplished by mounting or grasping the device by means of a suitable holder, which optionally may include a minute suction cup for engaging the outer surface of the insert. The holder may be one of the several types commonly used to insert and remove corneal contact lenses, artificial eyes, and the like. Further, the present invention contemplates the use of an indicator dye in the drug or material of the insert, or both, to serve as a visual indication as to the supply of drug within the device or the device itself in the eye. For this purpose, a small amount of methylene blue or any suitable dye material can be used.

The ocular inserts are suitably packaged using a drug and moisture impermeable packaging material such as the foil - polylaminates, e.g. aluminum foil - polyethylene laminate or aluminum foil - polyester (Mylar) - laminate. While the inserts can be packaged either wet or dry, the latter becomes mandatory when certain bioerosion processes are involved. More specifically, when the bioerosion process is effected by dissolution or hydrolysis, dry packing, e.g. vacuum packing, is required.

The ocular devices are preferably sterilized prior to insertion in the eye. The sterilization can be effected prior to packaging or after packaging. Suitable sterilization methods such as the use of radiation or ethylene oxide can be satisfactorily employed. Details for these methods and others are set forth in Remington's Pharmaceutical Sciences, Vol. XIV, 1970, pp. 1501-1518.

For a more complete understanding of the nature of this invention, reference should be made to the following examples which are given merely as further illustrations of the invention, and are not to be construed in a limiting sense. All parts are given by weight, unless stated to the contrary.

Example 1

A bioerodible ocular insert containing hydrocortisone is prepared in the following manner:

A. Preparation of zinc alginate -
1. Seven grams of sodium alginate (Keltone, Kelco Co., KT-9529-21) is dissolved in 350 ml of distilled water by means of efficient stirring, to yield a slightly viscous solution.
2. In a separate preparation, 10 grams of zinc chloride is dissolved in 600 ml of distilled water and the pH is adjusted to 3 by drop-wise addition of concentrated hydrochloric acid.
3. The zinc chloride is transferred into a gallon-size Waring blender and to this solution is added in small proportions the sodium alginate solution under moderate agitation. After the addition is complete, the mixture is vigorously stirred for 10-15 minutes, transferred to a glass container and allowed to stand overnight.
4. The precipitate is then transferred to a large size chromatographic column and washed continuously with distilled water to a negative silver chloride test (or to the same conductivity reading as distilled water). The aqueous suspension of the sodium chloride-free zinc alginate is isolated by lyophilization and vacuum-dried at 40° C overnight.

B. Preparation of hydrocortisone ocular insert -
1. The mixture containing 1.5 grams of micronized hydrocortisone in 3.5 grams of glycerine is homogenized by means of a suitable colloid mill or by simple grinding of the mixture with mortar and pestle.
2. The resulting white paste is slowly poured into a Waring blender containing 100 ml of 1.2% ammonium hydroxide solution under vigorous agitation. To this suspension is, then, added 5 grams of zinc alginate previously prepared, and the vigorous agitation is continued until the complete dissolution of the zinc alginate results; if marked thickening occurs, more ammonia solution can be added.
3. The viscous dispersion of (5) is drawn on a glass plate with a wet thickness of ca. 10 mils. The cast plate is placed in a circulating stream of warm, moisturized air at 40° C, and allowed to dry thoroughly.
4. The resulting film is removed from the plate by stripping, and is punch-cut into desired shape and size. For example, the circular insert device of 6.1 mm diameter and 3 mil thickness contains about 0.45 mg of hydrocortisone. When inserted in a monkey's eye, the resulting insert releases the drug over a two-day period at the termination of which the insert has totally eroded in the eye.

Example 2

A. Preparation of sodium alginate-hydrocortisone acetate ocular insert -
1. A paste containing 3.2 grams of micronized hydrocortisone acetate and 5.6g glycerine is prepared by grinding the mixture with mortar and pestle (or with colloid mill).
2. The paste is transferred into a Waring blender containing 0.03 gram Tween 80 (Atlas Chemical Industries) and 150 ml distilled water. To this fine particle suspension is added 7.5 grams of sodium alginate under vigorous stirring. Alternatively, the Premier-Dispersator (Premier Mill Corp.) may be used for this purpose. If necessary, the whole content may be transferred to a widemouth bottle and placed on a variable speed jar mill (Norton Co.) for 12 hours or to complete sodium alginate dissolution.
3. The film is then prepared by casting the mixture on a clean glass plate, and drying it at 40° C for 16 hours. A 125 mil cast of this solution gives about 10 mil-thick dry film.

B. Insolubilization -
1. The plasticized sodium alginate-hydrocortisone acetate film is dipped into 5.5% zinc chloride solution (pH adjusted to 4.5) for 5 hours. The film is then washed twice by immersion in a stirred 50% glycerine bath or until the final washing gives a negative silver chloride test. The film is then air-dried at room temperature, and punch-cut into circular disks 6 mm in diameter.
2. An aluminum alginate-hydrocortisone acetate film can also be prepared from the plasticized sodium alginate film by a method analogous to that of zinc alginate film described above using 10% alum ($KAl(SO_6)_2$) solution (pH 3.1).

When inserted in the sac of a human eye, the above prepared devices release the drug at a controlled rate. The inserts completely bioerode in the eye at the termination of the therapeutic program. Table I, which follows, characterizes the devices prepared.

TABLE I

| CHARACTERISTICS OF HYDROCORTISONE ACETATE CONTAINING METAL-ALGINATE COMPLEXES | | |
|---|---|---|
| | Zn-Alginate Hydrocortisone Acetate | Al-Alginate Hydrocortisone Acetate |
| 1. Hydrocortisone acetate content (H.C.Ac./Alg.) | 30/70 | 30/70 |
| 2. Cross-linking conditions | 5.5% $ZnCl_2$ pH 4.5 5 hrs. | 10% Alum pH 3.1 5 hrs. |
| 3. Tackiness | non-tack | non-tack |
| 4. Color, appearance, etc. | white, smooth | white, smooth |
| 5. Cohesiveness (or intactness on swelling, after 3-4 hrs.) | fair | good |
| 6. Time to erosion (days) | 6 days | >10 days |
| 7. Hydrocortisone acetate release µg/hr | 7 | 1.5 |

Example 3

Cross-linked gelatin ocular inserts containing hydrocortisone are used for the treatment of eye inflammation and are prepared as follows.

A phosphate buffer is prepared by addition of one liter of distilled water to 7.1 grams of disodium hydrogen phosphate and 6.9 grams of sodium dihydrogen phosphate monohydrate. The pH is determined to be 6.8. A solution of 0.9 gm glycerin in 40 ml of the phosphate buffer is prepared and 0.15 gm chlorobutanol is added. Upon heating to 90° C and stirring the chlorobutanol is dissolved. Nine grams of gelatin (Atlantic Pharmagel 250 Bloom Type A USP) is added slowly with stirring to the above prepared buffer solution at 90° C. Alternatively, to be more efficient, the gelatin can be added to the vigorously stirred buffer solution after it is cooled to room temperature and then the mixture heated at 90° C until solution is complete.

To suspend the hydrocortisone in the gelatin solution, 3.1 grams of hydrocortisone (Calibiochem) is first ground in a mortar and pestle, then 10 microliters of Tween 80 (Atlas, USP grade) are added and ground into the hydrocortisone. This mixture is suspended in five ml of phosphate buffer with thorough stirring and the resultant mixture added immediately to the stirred gelatin solution as it cools to approximately 50° C. The final mixture is stirred thoroughly for four minutes until the temperature falls to 40° C. It is then poured onto a sheet of polyvinyl chloride which is flattened against a glass plate after moistening the back with water. A film is cast with a doctor's blade adjusted for a wet thickness of 40 mils. The film is allowed to dry by standing at room temperature one day.

To cross-link the gelatin a solution of 1% formaldehyde by weight is prepared by addition of 13.1 grams of 38% formaldehyde reagent to 487 grams phosphate buffer (pH 6.8). This volume is sufficient for the treatment of the amount of film prepared as described above. The gelatin films are submerged in this buffered formaldehyde solution for 20 minutes at room temperature, the solution is discarded, and the films are rinsed with water quickly and soaked in ice water for 2 hours. After removal from the ice water and overnight standing at room temperature, the films are prepared for cutting by dipping in water for a few minutes. Excess water is removed and the inserts are cut from the flexible film with an illiptical die and dried at room temperature for several hours, then packaged in polyethylene-foil laminate packets. The ellipsoidal ocular inserts are 11.5 millimeters in length and 0.5 millimeter thick. When inserted in the sac of a human eye, the resulting insert relatively uniformly releases the drug over a period of 4 days, at which time the insert completely bioerodes.

Example 4

The following experiments illustrate the effect of the cross-linking agent, its concentration and time of treatment with blank gelatin inserts with regard to material bioerosion time.

Experimental Procedure

Standard gelatin formula:
18.0 gms Pharmagel Bloom Type A
1.8 gms Glycerin (Plasticizer)
0.3 gm Chlorobutanol (Preservative)
90 ml Phosphate Buffer (0.05M., pH 7.00)

Dissolve glycerin and chlorobutanol in preheated and cooled buffer. Add gelatin; dissolve by heating the solution. Films are made using the thin layer spreader yielding films that are approximately 17-19 mils thick. After spreading films, they are dried for 4 to 5 hours at room temperature.

The films are soaked in specific aldehyde concentration for a particular treatment time at 25° C. The gelatin films are washed with cold distilled water to remove excess aldehyde and are washed until the wash gives no color when tested with a chromo-tropic acid solution.

Alternatively, the cross-linking agent can be admixed with the gelatin prior to forming the film.

Inserts are made from a punch 11.5 × 4 mm, and one insert is placed in a glass-stoppered, graduated centrifuge tube containing 5 ml of 0.05M phosphate buffer, pH 7.00, at 37° C. The rate of dissolution is determined at 37° C according to the following procedure.

The insert is removed from the solution at selected intervals and the buffer solution is analyzed for gelatin content. The insert is then placed in another stoppered tube containing a fresh solution of buffer which is placed in the water bath. The procedure is repeatedly carried out.

The buffer solution that was removed is adjusted to 5 ml, if necessary, and read in Cary 14 Spectrophotometer set at wavelength 230 m$\mu$. Read sample versus a blank buffer solution. The absorbencies are recorded and totaled at each time interval. The percentage of gelatin released is obtained:

$$\frac{\text{Absorbency at time } t}{\text{Total absorbency}} \times 100 = \% \text{ Gelatin released}$$

A. Effect of formaldehyde concentration and time of treatment on the time of complete dissolution.

TABLE I

| | Treatment with Formaldehyde | |
|---|---|---|
| Formaldehyde Concentration (%) | Time of Treatment (hrs) | Time for Complete Dissolution (hrs) |
| 0.05 | .167 | 5 |
| | 2.0 | 51 |
| | 7.0 | 91 |
| | 24.0 | 151 |
| 1 | 5.0 | 119 |
| 2 | .083 | 16 |
| | .167 | 16 |
| | 2.0 | 197 |
| | 7.0 | 221 |
| | 24.0 | 241 |
| 2.5 | .083 | 16 |
| | .167 | 48 |
| 3 | .083 | 36 |
| | .167 | 46 |
| | .250 | 96 |
| 5 | .167 | 48 |
| | .25 | 72 |
| | .67 | 104 |
| | 2.0 | 197 |
| | 5.0 | 175 |
| | 7.0 | 221 |
| | 24.0 | 253 |
| 6 | .083 | 49 |
| 8 | .083 | 49 |
| 10 | .083 | 55 |
| | .167 | 72 |
| | .250 | 96 |
| | .167 | 72 |
| | .250 | 96 |
| | 2.0 | 197 |
| | 5.0 | 216 |
| | 7.0 | 216 |
| | 24.0 | 217 |
| 20 | .167 | 96 |
| | .250 | 168 |
| | .670 | 168 |
| 37 | .167 | 168 |
| | .250 | 168 |
| | .670 | 168 |

B. Effect of glutaraldehyde concentration and time of treatment on the time for complete dissolution of film (Table II).

TABLE II

| | Treatment with Glutaraldehyde | |
|---|---|---|
| Glutaraldehyde Concentration (%) | Time of Treatment (hrs) | Time for Complete Dissolution (hrs) |
| 0.01 | 7 | 78 |
| 0.05 | .083 | 42 |
| | .167 | 42 |
| | 7.0 | 334 |
| 0.025 | .167 | 192 |
| | 5.0 | 358 |

EXAMPLE 5

The following experimental procedure is used to determine the rate of release of hydrocortisone from an ocular insert.

Gelatin films containing 10% hydrocortisone acetate, based on total weight dry solids, are cross-linked in 1% aqueous formaldehyde for 20 minutes, immersed in ice water, and allowed to dry. Ocular inserts having an area of 1.1 cm$^2$ are cut from the films. The inserts are placed in open mesh Dacron packets which are suspended on a nichrome wire in 0.9% aqueous NaCl in volumetric flasks of appropriate size at 37° C, placed on a Burrel shaker, and agitated for varying periods. At the end of the indicated intervals, the packets are transferred to another volumetric flask and the washes are saved for analysis.

The saline washes are extracted by pouring them into a separatory funnel of appropriate volume, adding 40 ml diethyl ether to the volumetric flask, transferring the ether to the separatory funnel, shaking 100 times. After the separatory funnel is allowed to stand for 20 minutes, the saline layer is removed through the stop-cock, and the ether phase poured into a 25 × 200 mm culture tube. The saline phase is then transferred to the separatory funnel, 10 ml diethyl ether is added and the funnel shaken 100 times again. After allowing the separatory funnel to stand for 20 minutes, the saline phase is removed through the funnel stop-cock, and the ether phase is combined with the previous 40 ml extract by pouring it from the top of the funnel. The funnel is rinsed twice with 3 ml aliquots of diethyl ether, which is likewise transferred to the culture tube. The tube is placed in a mineral oil bath at about 35° C and the sample allowed to evaporate to dryness.

The residue is dissolved in 5 ml methanol, the tube fitted tightly with a black rubber stopper, shaken for 1 minute, allowed to stand for 2 hours at room temperature, shaken again for 1 minute, and transferred to a one cm spectrophotometer cell.

The resulting solution is scanned on a Cary-14 spectrophotometer from $\lambda = 250$ m$\mu$ to $\lambda = 235$ m$\mu$. Between samples, the sample cells were rinsed twice with methanol, once with acetonitrile, and once again with methanol. The sample cell is then filled with methanol, and balanced versus methanol at $\lambda = 242$ m$\mu$.

Calculations are made as follows:

$$\frac{\text{wt. of Hydrocortisone (Std. sol'n)}}{\text{wt. of Hydrocortisone (Sample)}} = \frac{\text{Absorbency (Std.)}}{\text{Actual absorbency (Sample)}}$$

Actual absorbency (Sample) - Absorbency at time × 5 (Dilution factor)

The data obtained over the first 7½ hours is as follows:

| Time (hrs) | Total Cumulative Amt Released (mg) |
| --- | --- |
| ½ | 175 |
| 1½ | 470 |
| 2½ | 750 |
| 4 | 1050 |
| 7½ | 1500 |

Although release studies were terminated after 7½ hours, data collected in subsequent studies indicate eventual complete release of drug.

EXAMPLE 6

Correlation between in vitro and in vivo bioerosion times in a rabbit's eye of a cross-linked gelatin matrix prepared in Example 1 as a function of formaldehyde concentration and time of treatment.

TABLE III

| Formaldehyde Concentration (%) | Time of Treatment (min) | Time for Complete Bioerosion (hrs) | Correlated In Vitro Bioerosion (hrs) |
| --- | --- | --- | --- |
| 5 | 40 | 90 | 96 |
| 6 | 5 | 18 | |
| | 6 | 18 | |
| | 20 | 60 | 60 |
| 10 | 20 | 24 | 70 |
| | 40 | 96 | 120 |
| 37 | 20 | 96 | 120 |

EXAMPLE 7

Results of a study of the erosion time of gelatin films treated with formaldehyde are set forth below.

Formaldehyde polymerization Gelatin films without drug are each treated with formaldehyde solutions buffered to pH 7.0, (3 mg of gelatin per 1 cc of solution) under the conditions shown in Table I. After cross-linking, the films are placed in several 100 cc ice water washes for 20 hours to remove free formaldehyde. The films are removed, dried at room temperature, and sterilized with ethylene oxide for 4 hours.

Results in TABLE 1 below demonstrate that the polymerization reaction is concentration, time and temperature dependent.

TABLE I

Formaldehyde Polymerization of Gelatin (without drug)

A. Effect of HCHO and Reaction Time — Erosion at 37° C

| (HCHO) | Reaction Time | Temperature | Daily Rate (est.) | Total Time |
| --- | --- | --- | --- | --- |
| 0.25% | 20 min | 25° C | 33% | 3 days |
| 0.50% | 20 min | 25° C | 19% | 5 days |
| 0.75% | 20 min | 25° C | 7.5% | Over 1 week |
| 1.0% | 20 min | 25° C | 7.5% | Over 1 week |
| 0.25% | 60 min | 25° C | 25% | 4 days |
| 0.50% | 60 min | 25° C | 5% | Over 1 week |
| 0.75% | 60 min | 25° C | 4% | Over 1 week |

B. Effect of Lowering Reaction Temperature

| 1.0% | 1/3 hour | 25° C | 33% | 3 days |
| 2.0% | 1 hour | 4.5° C | 25% | 4 days |
| 2.0% | 6 hour | 4.5° C | 3% | Over 1 week |

EXAMPLE 8

Erosion times for hydrocortisone acetate inserts as a function of formaldehyde and drug concentrations, reaction temperatures and time were studied.

Experimental

Gelatin (gelatin used is Pharmagel A grade, Atlantic Gelatin) films containing 80% by dry weight hydrocortisone acetate and 60% by dry weight hydrocortisone acetate were prepared by casting well stirred slurries of the drug in gelatin solutions onto a cellulose triacetate surface. Ocular insert sized pieces of this film were cross-linked in formaldehyde solutions at the indicated concentrations, all buffered at pH 7.0, using the same volume of formaldehyde solution for the same amount of film in each case. They were then washed in ice water for 18 hours to remove residual formaldehyde, dried at room temperature, and sterilized with ethylene oxide for 16 hours. To obtain drug release rate and insert erosion time, these were then placed in 150 milliliters of saline at 37° C and changed every few hours to fresh solutions. Selected samples of these solutions were analyzed for hydrocortisone acetate content by extracting with ether, evaporating the ether, dissolving the residue in methanol and either measuring the absorbency at 242 millimicrons or analyzing by liquid chromatography.

Results - Erosion Time and Drug Release

TABLE I

EROSION TIMES FOR HYDROCORTISONE ACETATE INSERTS AS A FUNCTION OF FORMALDEHYDE AND DRUG CONCENTRATIONS, REACTION TEMPERATURES AND TIME

| %HCHO | %Drug/%Gelatin | Reaction Temp. | Total Erosion Time in Days After HCHO Treatment For: | | | | |
| --- | --- | --- | --- | --- | --- | --- | --- |
| | | | ⅓ Hr. | 1 Hr. | 4 Hr. | 6 Hr. | 8 Hr. |
| 0.05 | 80/20 | 25° C | — | — | 3 | 4 | 5 + |
| 0.05 | 60/40 | 25° C | 1–2 days | 1–2 days | | 5 days | |
| 0.05 | 80/20 | 25° C | — | 0.1 days | | *6 + days | |
| 0.25 | 60/40 | 25° C | 1–2 days | 6 days | | 6 + days | |

TABLE I-continued

EROSION TIMES FOR HYDROCORTISONE ACETATE INSERTS AS A FUNCTION OF FORMALDEHYDE AND DRUG CONCENTRATIONS, REACTION TEMPERATURES AND TIME

| %HCHO | %Drug/%Gelatin | Reaction Temp. | Total Erosion Time in Days After HCHO Treatment For: | | | | |
|---|---|---|---|---|---|---|---|
| | | | ⅓ Hr. | 1 Hr. | 4 Hr. | 6 Hr. | 8 Hr. |
| 0.25 | 80/20 | 25° C | — | 4 ½ days | | 6 + days | |
| 0.50 | 60/40 | 25° C | 5 days | | | — | |
| 0.50 | 80/20 | 25° C | — | 6 + days | | 6 + days | |
| 0.75 | 60/40 | 25° C | 6 + days | 6 + days | | — | |
| 1.0 | 80/20 | 25° C | — | 6 + days | | 6 + days | |
| 0.25 | 60/40 | 4.5° C | — | — | | 5 days | |
| 0.25 | 80/20 | 4.5° C | — | 0.1 days | | 6 + days | |
| 0.50 | 60/40 | 4.5° C | — | 6 + days | | — | |
| 0.50 | 80/20 | 4.5° C | — | 4.3 days | | 5 days | |
| 0.75 | 80/20 | 4.5° C | — | 6 + days | | 6 + days | |
| 1.0 | 80/20 | 4.5° C | — | 6 + days | | 6 + days | |

*6+ days = Inserts lasting longer than 6 days when test was stopped.

TABLE II

HYDROCORTISONE ACETATE RELEASE RATES FROM ERODIBLE GELATIN INSERTS

| Polymerization Conditions | | | | Drug Release Rate (μg/hr) After: Hours | | | | | Total Erosion |
|---|---|---|---|---|---|---|---|---|---|
| % Drug | %HCHO | ° C | Time: | 18–24 | 24–29 | 42–47 | 66–71 | 90–95 | Time |
| 80 | 0.50 | 25 | 1 hour | 66 | — | 47 | 43 | 34 | 7 + days |
| 60 | 0.50 | 25 | 1 hour | — | 70 | — | — | — | 7 + days |
| 80 | 0.75 | 25 | 1 hour | 0 | — | 43 | 31 | 35 | 7 + days |
| 60 | 0.75 | 25 | 1 hour | — | 59 | — | — | — | 7 + days |
| 80 | 0.50 | 4 ½ | 1 hour | — | — | — | 46 | 96 | 4 days |
| 80 | 0.50 | 4 ½ | 1 hour | — | — | — | 50 | 70 | 4 days |

EXAMPLE 9

Five hundred grams of chloramphenicol of a particle size of 50 microns is encapsulated with polylactic acid polymer of molecular weight 50,000 according to the following procedure. Two hundred and fifty grams of the polylactic acid is dissolved into 2 liters of chloroform. The chloramphenicol particles are coated by polylactic acid using Wurster air suspension technique. The coat thickness is determined to be 30 microns thick.

A phosphate buffer is prepared by addition of one liter of distilled water to 7.1 grams of disodium hydrogen phosphate and 6.9 grams of sodium dihydrogen phosphate monohydrate. The pH is determined to be 6.8. A solution of 0.9 gram glycerin in 40 ml of the phosphate buffer is prepared and 0.15 gram chlorobutanol is added. Upon heating to 90° C and stirring, the chlorobutanol is dissolved. Nine grams of gelatin (Atlantic Pharmagel 250 Bloom Type A USP) is added slowly to the above prepared buffer solution at 90° C.

Three grams of the chloramphenicol microcapsules are dispersed in the above prepared gelatin solution as it cools to approximately 50° C. The final mixture is stirred thoroughly for 4 minutes until the temperature falls to 40° C. It is then poured onto a sheet of polyvinyl chloride which is flattened against a glass plate after moistening the back with water. A film is cast with a doctor's blade adjusted for a wet thickness of 40 mils. The film is allowed to dry by standing at room temperature 1 day.

To cross-link the gelatin a solution of 1% formaldehyde by weight is prepared by addition of 13.1 grams of 38% formaldehyde reagent to 487 grams phosphate buffer (pH 6.8). This volume is sufficient for the treatment of the amount of film prepared as described above. The gelatin films are submerged in this buffered formaldehyde solution for 20 minutes at room temperature, the solution is discarded, and the films are rinsed with water quickly and soaked in ice water for 2 hours. After removal from the ice water and overnight standing at room temperature, the films are prepared for cutting by dipping in water for a few minutes. Excess water is removed and the inserts are cut from the flexible film with an elliptical die and dried at room temperature for several hours. The ellipsoidal ocular inserts are 11.5 millimeters in length and 0.5 millimeter thick. When inserted in the sac of a human eye, the resulting insert continuously releases the drug at a controlled rate over a period in excess of 3 days and completely bioerodes in the eye thereafter.

EXAMPLE 10

The procedures and methods employed in Example 9 are repeated, however, substituting 3 grams of epinephrine microcapsules having an average particle size of 30 microns, coated to a 10 micron thickness with cholesterol palmitate for the 3 grams of chloramphenicol microcapsules used in Example 9. When placed in the eye, the above prepared insert continuously releases the drug at a controlled rate over a prolonged period of time and therafter completely bioerodes in the eye.

EXAMPLE 11

A bioerodible ocular insert containing hydrocortisone acetate is prepared in the following manner:
1. Ten grams of polyvinyl alcohol (duPont Elvanol 72-60, 99–100% hydrolyzed, molecular weight 250,000) is dissolved in 100 ml of deionized water at 90° C by means of Premier Dispersator (Premier Mill Corp.).
2. Into this hot solution is added slowly the hydrocortisone acetate paste which is prepared by mixing 2 grams of micranized hydrocortisone acetate, 5 grams of glycerine, and 0.01 gram of Tween 80 (Atlas) in colloid mill. The mixture is stirred until a homogeneous dispersion is obtained.
3. The presence of any bubbles in the mixture may be removed by means of centrifigation (N.B. prolonged centrifugation causes the settlement of hydrocortisone acetate) while the dispersion is cooled.
4. The dispersion is then drawn on a glass plate. The coated plates are thoroughly dried in a circulating stream of warm air at 50° C.
5. The resulting film is stripped off from the glass plate and punch-cut into circular inserts of 6 mm diameter and 0.5 mm thick. The device contains about 5 mg of hydrocortisone acetate per square centimeter. When inserted in a monkey's eye, the insert continuously releases the drug at a controlled rate over a prolonged period of time, and thereafter completely bioerodes in the eye.

EXAMPLE 12

A bioerodible ocular insert containing chloramphenicol is prepared in the following manner:
1. Poly(lactic acid) is prepared from the cyclic lactide as described by R. K. Kulkarni, E. G. Moore, A. F. Hegyelli, and F. Leonard in J. of Biomed. Mater., Res. 5, 169–181 (1971).
2. A solution of the polymer is prepard by dissolving 10 grams of the polymer in 100 ml methylene chloride.
3. To this solution is added 2.0 grams of chloramphenicol and the solution stirred until it is homogeneous.
4. The polymer and drug composition is drawn on a glass plate. The coated plate is first dried in air at room temperature and then placed in an oven at 40° C and allowed to dry thoroughly.
5. The resulting film is punch-cut into circular inserts of 6 mm diameter and 0.5 mm thick. The device contains about 8 mg of chloramphenicol per square centimeter. When inserted in a monkey's eye, the insert continuously releases the drug at a controlled rate over a prolonged period of time, and thereafter completely bioerodes in the eye.

EXAMPLE 13

A bioerodible ocular insert containing sulfathiazole is prepared in the following manner:
1. Poly(sebacic anhydride) is prepared from 20 grams of sebacic acid and 100 ml acetic anhydride as described in the book "Collected Papers of Wallace Hume Carothers", Interscience, New York, 1940, edited by H. F. Mark and S. B. Wentby.
2. Ten grams of the finely powdered polymer is then intimately mixed with 2.0 grams of sulfathiazole, the mixture compression molded on a Carver press, held at 90° C and 10,000 psi for 1 minute and then cooled to room temperature without releasing the pressure.
3. The resulting film is punch-cut into circular inserts of 6 mm diameter and 0.5 mm thick. The device contains about 8 mg of sulfathiazole per square centimeter. When inserted in a monkey's eye, the insert continuously releases the drug at a controlled rate over a 14-day period, and thereafter completely bioerodes in the eye.

EXAMPLE 14

A bioerodible ocular insert containing pilocarpine is prepared in the following manner:
1. Poly(glycolic acid) is prepared from hydroxyacetic acid as described by N. A. Higgins in U.S. Pat. No. 2,676,945 (Apr. 27, 1954).
2. A film having a thickness of 3 mils is compression molded on a Carver press held at 240° C and 20,000 psi.
3. A film of drum-containing core is prepared by:
    a. Dissolving 10 grams of poly(vinyl alcohol), duPont Elvanol 52–22 in 90 ml of distilled water maintained at 70° C.
    b. Cooling this solution, adding 20 grams of pilocarpine free base and stirring until solution is complete.
    c. Drawing this solution on a glass plate to provide a film having a thickness of 6 mils and drying in air at room temperature for 24 hours.
    d. Punch-cutting the pilocarpine-containing films into circular shapes of 4.5 mm diameter.
4. The circular core is placed between two sheets of poly(glycolic acid) prepared under (2) and heat sealed by a circular die of 6 mm diameter. The die temperature is 250° C and contact time 1 second. When insertd in a monkey's eye, the insert releases the drug over a prolonged period of time, and thereafter completely bioerodes in the eye.

EXAMPLE 15

Other ocular inserts of the type set forth in FIG. 3 include devices comprising the following combinations of drug, inner reservoir and outer rate controlling membrane:
1. An inner reservoir of hydrocortisone acetate dispersed in a poly(vinyl alcohol) matrix with the outer rate controlling membrane material being cross-linked gelatin.
2. An inner reservoir of chloramphenicol dispersed in a chitin matrix with polylactic acid being the outer rate controlling membrane material.
3. An inner reservoir of pilocarpine dispersed in a poly(vinyl pyrrolidone) matrix with the outer rate controlling membrane material being ethylene-maleic anhydride.

While there have been described and pointed out the fundamental novel features of the invention as applied to preferred embodiments, those skilled in the art will appreciate that various modifications, changes and omissions in the form and details of the ocular insert described can be made without departing from the spirit of the invention.

What is claimed is:
1. A bioerodible ocular device for the controlled continuous administration of a predetermined dosage of drug to the eye, comprising (1) an inner reservoir containing a drug formulation confined therein, and (2) an outer membrane formed from drug release rate controlling bioerodible material surrounding the inner reservoir, the membrane being permeable to passage of drug, but at a lower rate than through the inner reservoir, the device being of an initial shape which is adapted for insertion and retention in the sac of the eye bounded by the surfaces of the bulbar conjunctiva of the sclera of the eyeball and the palpebral conjunctiva of the lid, whereby release of drug from the device to the eye is effected primarily by a permeation control release mechanism in which the outer membrane continuously meters the flow of a therapeutically effective amount of drug from the reservoir to the eye at a controlled rate over a prolonged period of time, and wherein the device bioerodes in the environment of the eye concurrently with the dispensing or at a point in time after the dispensing of the therapeutically desired amount of drug.

2. The ocular device defined by claim 1 wherein the outer membrane material has a release rate to drug and an erosion rate in the eye such that the drug is essentially depleted from the inner reservoir prior to the substantially complete bioerosion of the membrane material.

3. The ocular device defined by claim 1 wherein the drug permeation rate through the inner reservoir is at least twice the permeation rate through the outer membrane.

4. The ocular device defined by claim 1 wherein the inner reservoir comprises a matrix material selected from the group consisting of solid matrix materials and microporous matrix materials having the drug dispersed therethrough.

5. The ocular device defined by claim 1 wherein the inner reservoir comprises a hollow container having the drug formulation confined therein.

* * * * *